(12) United States Patent
Brown et al.

(10) Patent No.: US 8,580,283 B2
(45) Date of Patent: Nov. 12, 2013

(54) GEL-BASED LIPSTICK HAVING IMPROVED RHEOLOGY

(75) Inventors: Steven E. Brown, New Windsor, NY (US); Arvind N. Shah, Suffern, NY (US)

(73) Assignee: Avon Products, Inc., New York, NY (US)

( * ) Notice: Subject to any disclaimer, the term of this patent is extended or adjusted under 35 U.S.C. 154(b) by 866 days.

(21) Appl. No.: 11/642,403

(22) Filed: Dec. 20, 2006

(65) Prior Publication Data

US 2008/0152679 A1 Jun. 26, 2008

(51) Int. Cl.
*A61K 8/37* (2006.01)
*A61K 8/92* (2006.01)
*A61Q 1/06* (2006.01)

(52) U.S. Cl.
CPC ... *A61K 8/92* (2013.01); *A61Q 1/06* (2013.01); *A61K 2800/00* (2013.01)
USPC .......................................................... 424/401

(58) Field of Classification Search
None
See application file for complete search history.

(56) References Cited

U.S. PATENT DOCUMENTS

| | | | |
|---|---|---|---|
| 4,832,944 A | 5/1989 | Socci et al. | |
| 5,340,569 A | 8/1994 | Elliott et al. | |
| 5,382,433 A * | 1/1995 | Pahlck et al. | 424/401 |
| 5,482,547 A | 1/1996 | Bugnon et al. | |
| 5,688,831 A | 11/1997 | El-Nokaly et al. | |
| 6,242,509 B1 * | 6/2001 | Berger et al. | 523/122 |
| 6,268,466 B1 | 7/2001 | MacQueen et al. | |
| 6,471,950 B1 | 10/2002 | Farer et al. | |
| 6,552,160 B2 | 4/2003 | Pavlin | |
| 6,592,857 B2 | 7/2003 | Lawson et al. | |
| 6,875,245 B2 * | 4/2005 | Pavlin | 44/275 |
| 2001/0049902 A1 | 12/2001 | Varadaraj et al. | |
| 2002/0006422 A1 | 1/2002 | Koda et al. | |
| 2003/0077240 A1 | 4/2003 | LeGrow et al. | |
| 2004/0018011 A1 | 1/2004 | Tomita | |
| 2004/0202622 A1 * | 10/2004 | Quadir | 424/59 |
| 2005/0191327 A1 * | 9/2005 | Yu et al. | 424/401 |
| 2005/0197479 A1 | 9/2005 | Pavlin | |
| 2006/0159643 A1 | 7/2006 | Jacquier | |
| 2006/0204461 A1 | 9/2006 | Pavlin | |

OTHER PUBLICATIONS

U.S. Appl. No. 11/642,348, filed Dec. 20, 2006, Arvind Shah et al.

* cited by examiner

*Primary Examiner* — Brian Gulledge
(74) *Attorney, Agent, or Firm* — David M. Joyal; Joan M. McGillycuddy

(57) ABSTRACT

Gel-based lipstick compositions are disclosed comprising an ester terminated poly(ester-amide) (ETPEA) polymeric gellant, a first wax component having a melting point above the sol-gel transition temperature of the ETPEA gellant, a second wax compositions having a melting point equal to of below the sol-gel transition temperature of the ETPEA gellant, optionally a silicone T-resin co-gellent, and one or more oils capable of forming a gel with the ETPEA gellant. The gel compositions are solid or semi-solid at room temperature and are capable of being molded into self-supporting sticks. The disclosed gels provide high gloss films when applied to the lips and/or provide a rheology characterized by a high viscosity over repeated shear cycles.

49 Claims, 5 Drawing Sheets

Gloss Comparison of Lip Products:
85 degree Angle Measurement

GEL-BASED LIPSTICK HAVING IMPROVED RHEOLOGY

FIELD OF INVENTION

The present invention relates generally to cosmetic compositions for the lips. More specifically, the invention relates to ester-terminated poly(ester-amide) ("ETPEA") gel-based compositions for imparting high gloss to the lips and/or for imparting films on the lips having enhanced rheological attributes of slip and feel.

BACKGROUND OF THE INVENTION

Conventional lipstick products typically comprise pigments and oils dispersed in a wax base. The wax base serves to provide the necessary stiffness and physical stability so that the composition can be in the form of a self-supporting stick desired by consumers. However, as a consequence of the high wax levels typically required to achieve these characteristics, conventional lipsticks suffer several disadvantages. Notably, they do not deliver a high gloss finish, are readily transferred from the lips to clothing, napkins, cups and the like, and exhibit undesirable bleeding of the pigments and oils from the product (syneresis). Recent approaches to overcoming some of the disadvantages of waxy lipsticks have centered primarily on the use of polymeric film formers in addition to, or as a partial replacement for, conventional waxy components in order to provide more robust films that are less prone to transfer and longer wearing. However, such products have heretofore not been able to achieve a high gloss, primarily because the opaque waxes dull the finish. Further, the wax structure of conventional lipsticks is known to break down under shear encountered during normal wear and rapidly lose the unctuous feeling of freshly applied product.

So-called "lip gloss" products are also known which deliver a glossy finish and maintain a satisfactory oily rheology during wear but are not durable and must be frequently reapplied to the lips to maintain the desired finish. Lip gloss products are typically transparent or translucent oil-based formulations which may also comprise low levels of colorant. High shine lip glosses are usually high viscosity liquids and therefore cannot be delivered in the convenient form of a self supporting stick but rather are packaged in tubes, pots, and the like and are typically applied to the lips with the fingers or an applicator.

There is a continuing need in the art for lip products, particularly lipsticks and lip glosses that overcome one or more of the foregoing deficiencies of conventional lip products. It would be desirable to combine the convenience and deep color of a lipstick with the high gloss and desirable rheology of a lip gloss to provide lip products, particularly pigmented lip products in stick form, which provide superior gloss, slip, feel, payoff, and/or wear. It is therefore an object of the invention to provide lip products in stick form which deliver a high gloss. It is yet another object of the invention to provide low-wax content lip products having a hardness sufficient for forming a self-supporting stick. It is a further object of the invention to provide lip products in stick form which have a rheology characterized by an unctuous feel which does not diminish during wear.

SUMMARY OF THE INVENTION

In accordance with the foregoing objectives and others, the present invention provides gel-based compositions which impart a high gloss film on the lips and/or provide an improved rheology. The gel-based compositions of the invention are capable of forming self-supporting solids or semi-solids at room temperature, even in the absence of substantial quantities of wax conventionally required to provide body to lipsticks. This property advantageously allows for the compositions to be formulated as low wax content lipsticks which further contributes to a high gloss finish, as conventional levels of waxes are known to diminish gloss. Further, the use of a gel-based matrix, rather than a wax-based matrix, provides a rheology characterized by a longer-lasting unctuous feel on the lips.

The compositions exhibit a gelled structure comprising a matrix of an ester terminated poly(ester-amide) polymer which is capable of gelling non-polar and low-polarity oils, such as hydrocarbons and fatty esters, alone or in combination with a silicone T-resin co-gellant. The compositions typically comprise a first wax component comprising at least one wax having a melting point above the sol-gel transition temperature $T_{gel}$ of the ester terminated poly(ester-amide) polymer and a second wax component having a melting point comparable to or below the sol-gel transition temperature $T_{gel}$ of the ester terminated poly(ester-amide) polymer. The combination of the gelled matrix with high and low melting point waxes contributes a desirable rheology characterized by a slip and feel heretofore only obtainable with liquid lip products. Further, the gel network is inherently transparent and thus the gloss of the oily components is not compromised.

In one aspect of the invention, compositions are provided for imparting an unctuous film to the lips comprising: (a) from about 0.1 to about 40% by weight of an ester terminated poly(ester-amide) polymer having an average molecular weight between about 3,000 and about 7,500 Daltons and being capable of forming a gel with low-polarity and nonpolar oils at or below a sol-gel transition temperature $T_{gel}$ wherein $T_{gel}$ is above body temperature; (b) from about 0.1 to about 20% by weight of a first wax component comprising one or more waxes having a melting point above $T_{gel}$; (c) from about 0.1 to about 20% by weight of a second wax component comprising one or more waxes having a melting point at or below $T_{gel}$; and (e) one or more low-polarity or nonpolar oils capable of forming a gel with the ester terminated poly(ester-amide) polymer at or below the sol-gel transition temperature $T_{gel}$; wherein the one or more low-polarity or nonpolar oils are selected from the group consisting of esters, hydrocarbons, and silicone-based oils; wherein the composition is characterized by a viscosity measured during a second shear cycle that is within ±20% of the viscosity measured during a first shear cycle at every shear rate between about 1 and about 10 sec$^{-1}$, wherein the first and the second shear cycles are identical and comprise increasing shear rates from about 1 to about 1,000 sec$^{-1}$. The compositions provide for enhanced rheological properties including slip and feel on application and during wear as compared to conventional wax-based lipsticks.

In another aspect, composition for imparting an unctuous film to the lips are provided comprising: (a) from about 0.1 to about 40% by weight Bis-Stearyl Ethylenediamine/Neopentyl Glycol/Stearyl Hydrogenated Dimer Dilinoleate copolymer having an average molecular weight between about 5,000 and about 6,000 Daltons and being capable of forming a gel with low-polarity and nonpolar oils at or below a sol-gel transition temperature $T_{gel}$ between about 70 and about 85° C.; (b) from about 0.1 to about 20% by weight of a first wax component comprising one or more waxes having a melting point above $T_{gel}$; (c) from about 0.1 to about 20% by weight of a second wax component comprising one or more waxes having a melting point at or below $T_{gel}$; and (e) one or more low-polarity or nonpolar oils capable of forming a gel with the ETPEA polymer at or below the sol-gel transition temperature $T_{gel}$; wherein said one or more low-polarity or nonpolar oils are selected from the group consisting of esters, hydrocarbons, and silicone-based oils; wherein the composition is characterized by a viscosity measured during a second shear cycle that is within ±20% of the viscosity measured during a first shear cycle at every shear rate between about 1 and about 10 sec$^{-1}$, wherein the first and said second shear cycles are identical and comprise increasing shear rates from about 1 to about 1,000 sec$^{-1}$; and wherein the composition is characterized by: (i) a viscosity greater than about 100 Pa·sec at shear rates between about 1 and about 5 sec$^{-1}$ when measured during the first and second shear cycles; and (ii) a viscosity greater than about 10 Pa·sec at shear rates between about 10 and about 50 sec$^{-1}$ when measured during the first and second shear cycles; and (iii) a viscosity greater than about 1 Pa sec at a shear rate of about 100 sec$^{-1}$ when measured during the first and second shear cycles.

Methods for imparting an unctuous film to the lips are also provided generally comprising applying to the lips any of the gel-based lipstick compositions described herein.

In a further aspect of the invention cosmetic compositions for imparting a film having improved rheology and/or imparting gloss to the lips are provided comprising: (a) from about 0.1 to about 40% by weight of an ester terminated poly(ester-amide) polymer ("ETPEA") having an average molecular weight between about 3,000 and about 7,500 Daltons and being capable of forming a gel with low-polarity and nonpolar oils at or below a sol-gel transition temperature $T_{gel}$, wherein $T_{gel}$ is above body temperature; (b) from about 0.1 to about 20% by weight of a first wax component comprising one or more waxes having a melting point above $T_{gel}$; (c) from about 0.1 to about 20% by weight of a second wax component comprising one or more waxes having a melting point comparable to, equal to, or below $T_{gel}$; (d) from about 0.1 to about 25% by weight of a silicone T-resin having a refractive index of at least 1.43 when measured as a film at 25° C.; and (e) one or more low-polarity or nonpolar oils which are capable of forming a gel with the ETPEA polymer at or below the sol-gel transition temperature $T_{gel}$ of the ETPEA polymer. Typically, the one or more low-polarity or nonpolar oils are selected from the group consisting of fatty esters, hydrocarbons, and silicone-based oils, and combinations thereof.

In another aspect of the invention, cosmetic compositions for imparting a film having improved rheology and/or imparting gloss to the lips are provided as self-supporting compositions, without the need for high levels of wax, i.e., greater than about 12% by weight, required in conventional formulations. The cosmetic compositions according to this aspect of the invention comprise: (a) from about 0.1 to about 40% by weight of the ETPEA polymer having the INCI name Bis-Stearyl Ethylenediamine/Neopentyl Glycol/Stearyl Hydrogenated Dimer Dilinoleate copolymer and having an average molecular weight between about 3,000 and about 7,500 Daltons and being capable of forming a gel with low-polarity and nonpolar oils at or below a sol-gel transition temperature $T_{gel}$ of the ETPEA polymer, wherein $T_{gel}$ of the ETPEA polymer is between about 70° C. and about 85° C.; (b) from about 0.1 to about 12% by weight of a first wax component comprising one or more waxes having a melting point above about $T_{gel}$ of the ETPEA polymer and below about 110° C.; (c) from about 0.1 to about 12% by weight of a second wax component comprising one or more waxes having a melting point comparable to, equal to, or below $T_{gel}$ of the ETPEA polymer and above about 45° C.; (d) from about 0.1 to about 25% by weight of an alkyl phenyl silsesquioxane T-resin having a refractive index of at least 1.43 when measured as a film at 25° C.; wherein the at least one alkyl phenyl silsesquioxane resin comprises siloxy moieties:

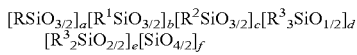

$$[RSiO_{3/2}]_a[R^1SiO_{3/2}]_b[R^2SiO_{3/2}]_c[R^3{}_3SiO_{1/2}]_d$$
$$[R^3{}_2SiO_{2/2}]_e[SiO_{4/2}]_f$$

where R is methyl; $R^1$ is $C_{2\text{-}20}$ alkyl or $C_{5\text{-}20}$ cycloalkyl; $R^2$ is phenyl, $R^3$ is $C_{1\text{-}20}$ alkyl, $C_{5\text{-}20}$ cycloalkyl, $C_{7\text{-}14}$ aralkyl, $C_{7\text{-}14}$ alkaryl, or $C_{6\text{-}10}$ aryl; and a, b, and c are such that their respective siloxy groups together comprise at least 90 mol percent of the total of siloxy moieties, and d, e, and f are such that their respective moieties together comprise less than 10 mol percent of all of siloxy moieties; and (e) one or more low-polarity or nonpolar oils capable of forming a gel with the ETPEA polymer at or below the sol-gel transition temperature $T_{gel}$ of the ETPEA polymer wherein the one or more low-polarity or nonpolar oils are selected from the group consisting of fatty esters, hydrocarbons, and silicone-based oils. Preferably, the first and second wax components collectively comprise about 12% or less by weight of said composition, i.e., below conventional wax levels for a lipstick. The composition is nevertheless self-supporting at room temperature such that it is capable of being formulated as a lipstick and the like. The composition has a hardness at room temperature of at least 40 g.

In yet another aspect of the invention, cosmetic compositions for imparting a film having improved rheology and/or imparting gloss to the lips are provided comprising: (a) from about 0.1 to about 40% by weight of the ETPEA polymer having the INCI name Bis-Stearyl Ethylenediamine/Neopentyl Glycol/Stearyl Hydrogenated Dimer Dilinoleate copolymer and having an average molecular weight between about 5,000 and about 6,000 Daltons and being capable of forming a gel with low-polarity and nonpolar oils at or below a sol-gel transition temperature $T_{gel}$ of the ETPEA polymer between 70 and about 85° C.; (b) from about 0.1 to about 20% by weight of a first wax component comprising one or more waxes selected from the group consisting of linear polyethylene wax, microcrystalline petroleum wax, and combinations thereof; (c) from about 0.1 to about 20% by weight of a second wax component comprising ozokerite wax; (d) from about 0.1 to about 25% by weight of a phenyl silsesquioxane T-resin having a refractive index of at least 1.50 measured as a film at 25° C.; (e) one or more low-polarity or nonpolar oils capable of forming a gel with the Bis-Stearyl Ethylenediamine/Neopentyl Glycol/Stearyl Hydrogenated Dimer Dilinoleate copolymer at or below the sol-gel transition temperature $T_{gel}$; wherein the one or more low-polarity or nonpolar oils are selected from the group consisting of fatty esters, hydrocarbons, and silicone-based oils; and (f) from 0.1 to about 10% by weight of one or more pearling agents; wherein said composition exhibits a gloss across the entire range of 0.1 to about 10% by weight one or more pearling agents within about 10% of the gloss of an otherwise identical composition in the absence of said one or more pearling agents, as measured at an angle of 850. The composition typically has a hardness at room temperature of at least 40 g, but preferably will have a substantially greater hardness, typically between about 200 and about 300 g. Surprisingly, even such relatively hard sticks have excellent "pay off" such that upon application to the lips an acceptable amount of product is transferred to the lips.

Methods for imparting high gloss to the lips are also provided comprising applying the inventive compositions to the lips. The compositions typically have a gloss of at least about 65, more typically at least about 70, preferably at least about 75, and more preferably at least about 80, when measured at 85 degrees. In some embodiment of the invention, the compositions will have a gloss of about 85 or greater, about 90 or greater, or about 95 or greater when measured at 85 degrees.

While the preferred lipsticks according to the invention have both improved rheology and impart high gloss, it will be understood that, in the broadest aspect, the invention is not limited to any particular gloss level, as the improved rheology will find significant application regardless of gloss. Further, while the preferred embodiments of the invention involve compositions having a hardness suitable for formulating the compositions in stick form, the invention is not so limited and embraces compositions of any hardness, including liquids, viscous liquids, semi-solids, and solids, as the improved rheological attributes described herein are contemplated to benefit liquid lip gloss products as well as lipsticks.

These and other aspects of the invention will be better understood by reference to the following Detailed Description, including the Figures and appended claims.

DETAILED DESCRIPTION

Figure 1:
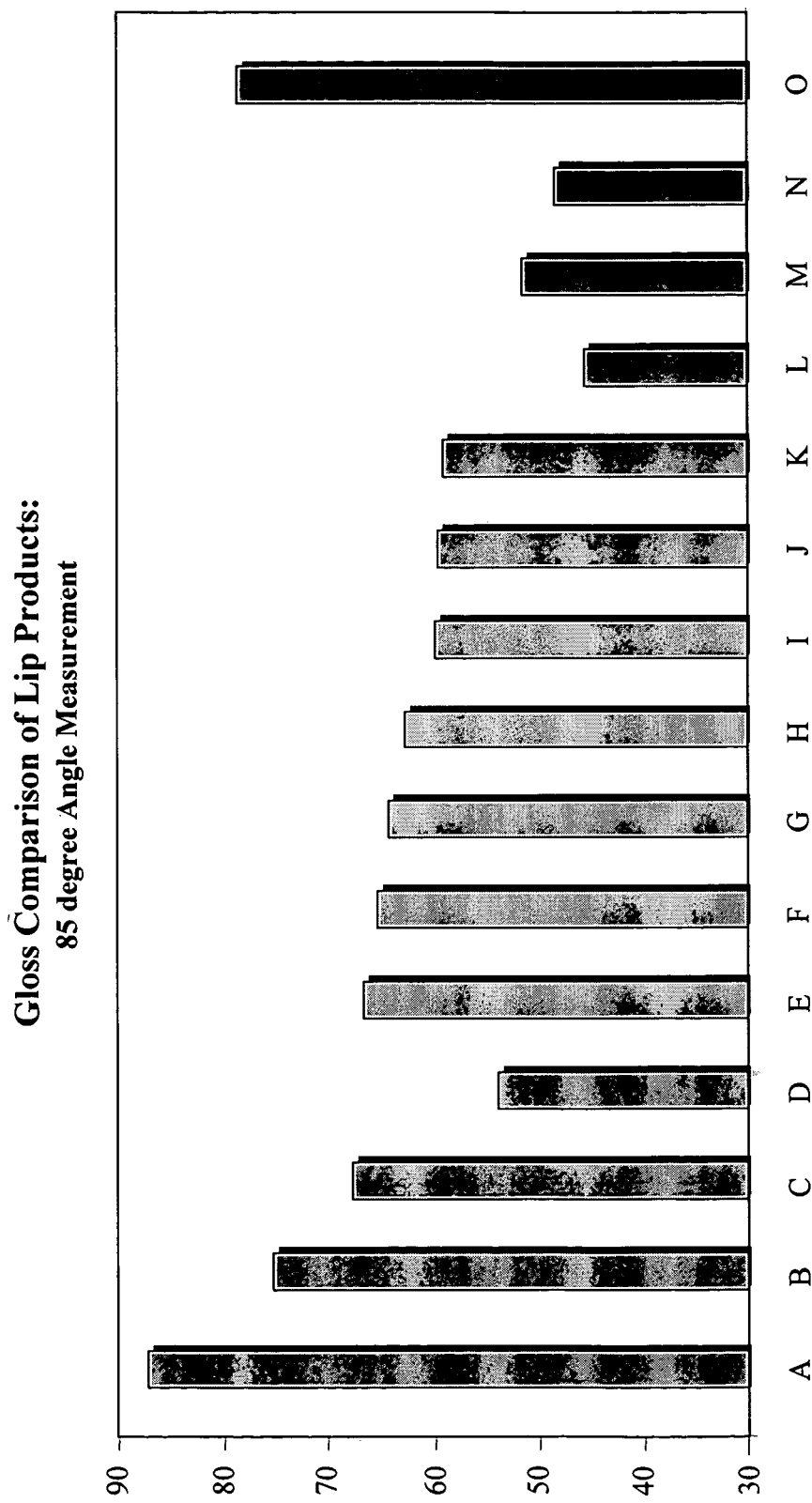
FIG. 1 compares the 85 degree gloss of a lipstick according to the invention (A) with the gloss of liquid lip gloss product (B), several commercially available wax-based lipsticks (C-N), and a two-part lip product having a transparent top coat (O).

As used herein, all terms are intended to have their ordinary and accustomed meaning in the art unless otherwise explicitly defined.

The present invention is founded on the discovery that the use of ester terminated poly(ester-amide) ("ETPEA") polymers in combination with certain co-gellants and waxes in cosmetic compositions, such as lipsticks and the like, provide products having high gloss and superior rheology. In addition to the ETPEA polymer, the compositions typically comprise a co-gellant, ideally a high molecular weight silicone T-resin, a first wax component and a second wax component. The first wax component comprises at least one wax having a melting point above the sol-gel transition temperature $T_{gel}$ of the ETPEA polymer and the second wax component comprises at least one wax having a melting point comparable to, equal to, or below the sol-gel transition temperature $T_{gel}$ of the ETPEA polymer.

As used herein, the term "comparable to," when used in reference to the melting point of the second wax component, means that the melting point range of the wax may, at the upper end or the melting range, be somewhat greater than $T_{gel}$ of the ETPEA polymer, but in no event greater than about 6° C., preferably no greater than about 3° C., and more preferably, no greater than about 1° C. The importance being that as the composition is cooled from an initial liquid state at high temperature, the second wax component begins to crystallize or otherwise solidify simultaneously with, or after, the onset of gellation of the ETPEA polymer such that the second wax component is constrained within the gel network of the ETPEA polymer, preferably, but not necessarily, as a microdispersion. Because the first wax component crystallizes or otherwise solidifies above $T_{gel}$ of the ETPEA polymer, no such constraint on its solidification is imposed by the composition.

The ETPEA polymer and both wax components are selected such that $T_{gel}$ of the ETPEA polymer and the melting point of both the first and second wax components are above room temperature (about 23° C.) and, preferably, above body temperature (about 36-38° C.), such that the ETPEA polymer remains gelled and the waxes remain solid during wear, i.e., when applied as a film to the lips, and during storage under ambient conditions.

In one embodiment, the cosmetic compositions for imparting a film having improved rheology and/or imparting gloss to the lips will comprise:

(a) from about 0.1 to about 40% by weight of an ester terminated poly(ester-amide) polymer having an average molecular weight between about 3,000 and about 7,500 Daltons and being capable of forming a gel with low-polarity and nonpolar oils at or below a sol-gel transition temperature $T_{gel}$ wherein $T_{gel}$ is above body temperature;

(b) from about 0.1 to about 20% by weight of a first wax component comprising one or more waxes having a melting point above $T_{gel}$;

(c) from about 0.1 to about 20% by weight of a second wax component comprising one or more waxes having a melting point at or below $T_{gel}$;

(d) from about 0.1 to about 25% by weight of a silicone T-resin and a refractive index of at least 1.43 measured as a film at 25° C.;

(e) one or more low-polarity or nonpolar oils soluble capable of forming a gel with said ester terminated poly (ester-amide) polymer at or below said sol-gel transition temperature $T_{gel}$; wherein said one or more low-polarity or nonpolar oils are selected from the group consisting of esters, hydrocarbons, and silicone-based oils;

wherein the composition has a gloss of at least about 70 (preferably at least 75, 80, or 85) when measured at 85 degrees. As shown in FIG. 1, the lipstick compositions of the invention, indicated by "A," provide higher gloss than commercially available wax-based lipsticks (labeled C-N and identified elsewhere herein), as well as a representative liquid lip gloss ("B") and a two-part lipstick comprising a clear top coat ("O").

The various components of the composition are described below.

ETPEA Polymer

The ETPEA polymer is a necessary component of the inventive compositions. In the broadest aspects, any ETPEA polymer compatible with cosmetic use is contemplated to be suitable, provided the polymer is capable of existing as a gel at room temperature and, preferably, at body temperature. In that regard, the sol-gel transition temperature $T_{gel}$ of the ETPEA polymer is typically above about 40° C., more typically, above about 50° C., preferably above about 60° C., and more preferably above about 70° C. In a currently preferred embodiment, the ETPEA polymer has a $T_{gel}$ between about 70° C. and about 85° C., including a representative embodiments having a $T_{gel}$ of about 70° C., about 75° C., about 80° C., and about 85° C. While not strictly identical, the softening point, as measured by, for example, differential scanning calorimetry (DSC), of the ETPEA polymer will provide useful for approximating the sol-gel transition temperature $T_{gel}$ as this is the point where the hydrogen bonding network of the polymer gel begins to break down. In some embodiments, the ETPEA polymer will have a softening point of between about 70° C. and about 85° C., including about 70° C., about 75° C., about 80° C., and about 85° C.

Non-limiting examples of suitable ETPA polymers and methods of making the same are described in U.S. Pat. Nos. 6,552,160 and 6,875,245, the disclosures of which are hereby incorporated by reference in their entirety.

Generally, the ETPA polymer may be a random, alternating, or block copolymer comprising units A and B attached to one another through ester and/or amide linkages and terminated by ester linkages to a terminating groups, wherein:

(a) unit A has the structure:

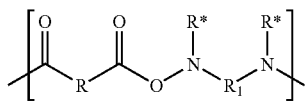

wherein,

R is a linear, branched, or cyclic alkyl group having from 4 to 70 carbon atoms, optionally comprising: (i) one or more unsaturated bonds; (ii) one or more aliphatic or aromatic rings; and/or (iii) one or more heteroatoms selected from the group consisting of halogen, oxygen, nitrogen, and sulfur; and wherein R optionally comprises one or more groups —(C=O)—O— linking R to additional units of A or B; wherein R is independently selected at each occurrence of unit A; and $R_1$ is a radical having from 2 to 36 carbon atoms selected from the group consisting of linear, branched, or cyclic alkyl groups, aryl groups, or heteroaryl groups, and combinations thereof, optionally comprising: (i) one or more unsaturated bonds; (ii) one or more aliphatic or aromatic rings; and/or (iii) one or more heteroatoms selected from the group consisting of halogen, oxygen, nitrogen, and sulfur; wherein $R_1$ is independently selected at each occurrence of unit A;

R* is independently selected, at each occurrence, from hydrogen, aryl, and linear, branched, or cyclic alkyl group having from 1 to 10 carbon atoms, optionally comprising: (i) one or more unsaturated bonds; (ii) one or more aliphatic or aromatic rings; and/or (iii) one or more heteroatoms selected from the group consisting of halogen, oxygen, nitrogen, and sulfur; and wherein independently each R* may, together with $R_1$ or with the other R*, form a heterocyclic ring;

(b) unit B has the structure:

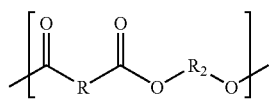

wherein R is as defined above and is independently selected at each occurrence of B, and $R_2$ is a linear, branched, or cyclic alkyl group having from 2 to 20 carbon atoms, optionally comprising: (i) one or more unsaturated bonds; (ii) one or more aliphatic or aromatic rings; and/or (iii) one or more heteroatoms selected from the group consisting of halogen, oxygen, nitrogen, and sulfur; and wherein $R_2$ may optionally comprise between 1 and 4 groups of the form —O— linking $R_2$ to additional units of A or B; wherein $R_2$ is independently selected at each occurrence of unit B; and (c) terminal groups of the form $R_3O$— form an ester linkage with the terminal carbonyl group of unit A and/or unit B, wherein $R_3$ is independently, at each terminal group, a linear, branched, or cyclic alkyl group having from 10 to 30 carbon atoms, optionally comprising: (i) one or more unsaturated bonds; (ii) one or more aliphatic or aromatic rings; and/or (iii) one or more heteroatoms selected from the group consisting of halogen, oxygen, nitrogen, and sulfur.

In some embodiments, R is the same at each occurrence of units A and/or B in the polymer. In other embodiments, R may be different at one or more occurrences of units A and/or B. Likewise or $R_1$ and/or $R_2$ are preferably the same at each occurrence of units A and/or B in the polymer, but may also be different at each occurrence. By the phrase "at each occurrence of unit A" is meant that, of the plurality of units of A contained in the polymer, any given unit A may be different from one or more other units of A by virtue of the selection of R and $R_1$. Likewise, the phrase "at each occurrence of unit B" means that of the plurality of units of B contained in the polymer, each individual unit B may be different from one or more other units of B by virtue of the selection of R and $R_2$. That is, for example, if $R_1$ is a group —$CH_2$—$CH_2$—, each instance of unit A may contain the same group —$CH_2$—$CH_2$— for $R_1$ or may contain different groups for $R_1$. For example, $R_1$ may be a group —$CH_2$—$CH_2$— at some instances of unit A and a group, for example, —$CH_2$—$(CH_2)_{1-4}$—$CH_2$—, at other occurrences of unit A. In one embodiment, one or more of R, $R_1$, and $R_2$ is the same at every occurrence of units A and/or B in the polymer.

In the preferred ETPEA polymers according to the invention, at one or more occurrence of unit A, each R* is hydrogen and $R_1$ is a group —$(CR'R'')_n$— wherein n is an integer from 2 to 12, and R' and R'' are independently at each occurrence selected from the group consisting of hydrogen, methyl, ethyl, propyl, and butyl. In a preferred embodiment, $R_1$ is —$(CH_2)_2$— at every occurrence of unit A. In other embodiments, $R_1$ is —$(CH_2)_2$— in at least 80%, preferably at least 90% and more preferably at least 95% of the occurrences of unit A.

Preferably $R_2$, at one or more occurrence of unit B, is selected from the group consisting of —$(CH_2)_n$—, —$CH_2$—CR'H—, and —$CH_2$—CR'R''—$CH_2$—, wherein n is an integer from 2 to 6, R' and R'' are independently hydrogen or an alkyl or aryl group having from 1 to 12 carbon atoms and optionally comprising between 1 and 4 groups of the form —O— linking R' and/or R'' to additional units of A or B and/or optionally including one or more groups of the form —OH. In a preferred embodiment $R_2$, at one or more occurrence of unit B, is a divalent neopentyl group (neopentylene), including groups of the form —CH$_2$—C(CH$_3$)$_2$—CH$_2$—.

In a preferred embodiment, R$_1$ is —(CH$_2$)$_2$— in at least 95% and preferably in each of the occurrences of unit A and R$_2$ is —CH$_2$—C(CH$_3$)$_2$—CH$_2$— in at least 95% and preferably in each of the occurrences of unit B.

Preferably, at one or more occurrence of unit A and/or unit B, R is independently at each occurrence, a group having the structure:

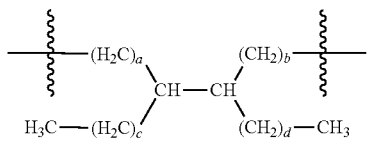

wherein a, b, c, and d are independently integers from 1 to 20. One skilled in the art will appreciate that groups of this form correspond to the alkyl portion of hydrogenated fatty acid dimers, such as the reaction product formed by heating C$_{18}$ unsaturated fatty acids (oleic, linoleic, linolenic acids and the like) in the presence of a clay catalyst followed by hydrogenation. Stated in another way, R may be selected, independently at each occurrence, from divalent alkyl groups corresponding to the alkyl portion (i.e., excluding the —C(=O)—OH functional groups) of dimer acids formed by the dimerization reaction of unsaturated fatty acids having from 5 to 30 carbon atoms, preferably C$_{18}$ unsaturated fatty acids such as oleic, linoleic, linolenic, and tall oil fatty acids.

In one embodiment, the ETPEA polymer is a random copolymer comprising n equivalents of unit A and m equivalents of unit B, wherein n and m are selected to provide a polymer having an average molecular weight between about 3,000 and about 7,500 Daltons. Preferably, n and m are selected to provide a polymer having an average molecular weight between about 5,000 and about 6,000, and more preferably about 5,500 Daltons.

Suitable ETPEA polymers may be prepared from dibasic acid, diamine, polyol and monoalcohol components, as described, for example, in U.S. Pat. No. 6,552,160, the disclosure of which is hereby incorporated by reference. Briefly, ETPEA polymers may be prepared by reacting w equivalents of hydroxyl from polyol or a reactive equivalent thereof, x equivalents of carboxylic acid from diacid or a reactive equivalent thereof, y equivalents of amine from diamine, and z equivalents of hydroxyl from monoalcohol or a reactive equivalent thereof; wherein w/(w+y+z) is within the range of about 0.05 to 0.45; y/(w+y+z) is within the range of about 0.25 to 0.75; and z/(w+y+z) is within the range of 0.20 to 0.50; under reactions conditions to provide a resin composition having an acid number of less than 20 and an amine number of less than 20, wherein at least about 50% of the carboxylic acid equivalents are from polymerized fatty acid, at least about 50% of the amine equivalents are from ethylene diamine, and mono-alcohol is substantially the only monofunctional reactant used to form the resin. Preferably, 10-60 equivalent percent of the total of the hydroxyl and amine equivalents provided by diamine, polyol and monoalcohol are provided by monoalcohol; and no more than 50 equivalent percent of the total of the hydroxyl and amine equivalents provided by diamine, polyol and monoalcohol are provided by polyol. Preferably, polymerized fatty acid constitutes at least 75 equivalent percent, and more preferably, at least about 90 equivalent percent of the acid equivalents of the dibasic acid. Ethylene diamine preferably constitutes at least about 70 equivalent percent of the amine equivalents from diamine.

The selection of dibasic acid, diamine, polyol and monoalcohol is preferably as described in U.S. Pat. No. 6,552,160, the disclosure of which is hereby incorporated by reference. Briefly, preferred dibasic acids are polymerized fatty acids formed from oleic acid, linoleic acid, linolenic acid, tall oil fatty acid and the like. The polymerized fatty acid is preferably hydrogenated before use. Preferably, the diamine reactant is ethylene diamine. Preferred monoalcohol (i.e., monohydric alcohol) reactants include formula R$_3$OH, wherein R$_3$ is preferably a hydrocarbon group having at least ten carbon atoms, such as, for example, 1-dodecanol, 1-tetradecanol, 1-hexadecanol (cetyl alcohol), 1-octadecanol (stearyl alcohol), 1-eicosanol (arachidyl alcohol) and 1-docosanol (behenyl alcohol), and the like. Preferred polyols include without limitation ethylene glycol, propylene glycol, butylene glycol, glycerol, trimethylolpropane, pentaerythritol, neopentyl glycol, tris(hydroxylmethyl)methanol, di-pentaerythritol, and tri-pentaerythritol, and the like. In addition to polymerized fatty acids and ethylene diamine, other diacids and diamines may also be present. Suitable "co-diacids" and "co-diamines" include, but are not limited to, those described in U.S. Pat. No. 6,552,160, incorporated herein by reference.

The currently preferred ETPEA polymer according to the present invention is, according to the nomenclature of INCI, a Bis-Stearyl Ethylenediamine/Neopentyl Glycol/Stearyl Hydrogenated Dimer Dilinoleate copolymer, commercially available from Arizona Chemical (Jacksonville, Fla.) under the tradename SYLVACLEAR® C75V. This polymer is characterized by: a softening point between 75-85° C. as measured by the Ring & Ball method of ASTM E28-99, incorporated by reference herein; an acid number of 26 (maximum) as measured by ASTM D803, D65 and D1980, incorporated by reference herein; an amine number of 1 (maximum) as measured by ASTM D2073 and D2074, incorporated by reference herein; and an average molecular weight of about 5,500 Daltons.

The ETPEA polymer may suitable comprise from about 0.1 to about 40% by weight of the composition, but typically will comprise between about 0.1 to about 25% by weight of the composition. In some embodiments, the ETPEA polymer will comprise from about 0.5 to about 15% by weight of the composition or from about 0.5 to about 12%. In some embodiments, the ETPEA polymer will comprise less of the composition than the lipstick formulations disclosed in U.S. Patent Pub. No. 2005/0197479 to Pavlin, the disclosure of which is hereby incorporated by reference. The lipstick formulations described in U.S. Patent Pub. No. 2005/0197479 to Pavlin typically comprise ETPEA polymer from 15-25% by weight, including several examples of ETPA polymer levels of 18% by weight. Accordingly, in some embodiments the inventive compositions will comprise from 0.1% to less than about 12, 10, 8, 6, or about 5% by weight ETPEA polymer. In other embodiments, the inventive compositions will contain as little as 0.1 to about 2.5% by weight ETPEA polymer, 0.1 to about 2% by weight ETPEA polymer, 0.1 to about 1.5% by weight ETPEA polymer, or 0.1 to about 1% by weight ETPEA polymer. In one interesting variant, the ETPEA polymer will comprise from 0.5 to 1% by weight, or 0.5 to less than 1% by weight of the composition. Suitable lipsticks can been prepared from compositions comprise from 0.1-1%, 1-2%, 2-3%, 3-4%, 4-5%, 5-6%, 6-7%, 7-8%, 8-9%, 9-10%, 10-11% or 11-12% by weight ETPEA polymer, each range being considered a separate embodiment of the invention. In one representative embodiment, the compositions will comprise between about 5 and about 6% by weight ETPEA polymer. The compositions of the present invention are believed to provide superior gloss and/or hardness and/or rheology to the lipstick formulations of U.S. Patent Pub. No. 2005/0197479.

Waxes

The first wax component may comprise any wax, particularly those typically used in lipsticks and other cosmetic products, provided the melting point of the wax is greater than the $T_{gel}$ of the ETPEA polymer. Similarly, the second wax component may comprise any cosmetically acceptable wax provided that the melting point of the wax is comparable to, equal to, or below the $T_{gel}$ of the ETPEA polymer.

The waxes may be natural, mineral and/or synthetic waxes. Natural waxes are those of animal origin, including without limitation beeswax, spermaceti, lanolin, and shellac wax, and those of vegetable origin, including without limitation carnauba, candelilla, bayberry, and sugarcane wax.

Mineral waxes contemplated to be useful include, without limitation ozokerite, ceresin, montan, paraffin, microcrystalline, petroleum, and petrolatum waxes.

Synthetic waxes include, for example, polyethylene glycols such as PEG-18, PEG-20, PEG-32, PEG-75, PEG-90, PEG-100, and PEG-180 which are sold under the tradename Carbowax® (The Dow Chemical Company). Mention may be made of Carbowax 1000 which has a molecular weight range of 950 to 1,050 and a melting point of about 38° C., Carbowax 1450 which has a molecular weight range of about 1,305 to 1,595 and a melting point of about 56° C., Carbowax 3350 which has a molecular weight range of 3,015 to 3,685 and a melting point of about 56° C., and Carbowax 8000 which has a molecular weight range of 7,000 to 9,000 and a melting point of about 61° C.

Synthetic waxes also include Fischer Tropsch (FT) waxes and polyolefin waxes, such as ethylene homopolymers, ethylene-propylene copolymers, and ethylene-hexene copolymers. Representative ethylene homopolymer waxes are commercially available under the tradename POLYWAX® Polyethylene (Baker Hughes Incorporated) with melting points ranging from 80° C. to 132° C. Commercially available ethylene-α-olefin copolymer waxes include those sold under the tradename PETROLITE® Copolymers (Baker Hughes Incorporated) with melting points ranging from 95° C. to 115° C.

Table 1 provides several suitable waxes arranged by melting point or melting range.

TABLE 1

| Wax | Melting Point (° C.) |
| --- | --- |
| acrawax | 140 |
| microcrystalline petroleum wax | 99 |
| linear polyethylene wax | 95 |
| stearone | 89 |
| castor wax | 86 |
| montan wax | 82-95 |
| lignite wax | 82-95 |
| ouricouri wax | 81-84 |
| carnauba wax | 78-85 |
| rice bran wax | 77-86 |
| shellac wax | 74-78 |
| esparto wax | 73 |
| ozokerite wax | 72 |
| jojoba wax | 70 |
| candelilla wax | 68-73 |
| ceresin wax | 67-71 |
| beeswax | 62-64 |
| castor wax | 60 |
| sugarcane wax | 60 |
| stearyl alcohol | 59 |
| hard tallow | 57-60 |
| cetyl alcohol | 56 |
| petrolatum | 54 |
| glyceryl monostearate | 54-56 |
| Japan wax | 53 |
| silicone waxes | 53-75 |
| paraffin wax | 50-60 |
| lanolin alcohol | 45-60 |
| bayberry wax | 45 |
| cetyl palmitate | 43-53 |
| lanolin | 38-42 |
| illipe butter | 34-38 |
| cocoa butter | 31-35 |

It will be understood that the melting points and ranges provided in Table 1 are merely representative of typical values for each wax and wide variation in the melting point or melting point range may be observed from sample to sample depending on the source and purity of the wax. Thus, for example, ozokerite wax is considered to be useful in the practice of the invention regardless of whether its melting point is determined to be 72° C. or otherwise. It is within the skill in the art to determine the melting point or melting point range of any given wax sample. Melting points may be determined, for example, by drop melting point according to ASTM D127, incorporated by reference herein, and/or ring-and-ball softening point according to ASTM D36, incorporated by reference herein.

In a preferred embodiment where the ETPEA polymer has a sol-gel transition temperature $T_{gel}$ of about 70° C. to about 85° C., the first wax component comprises one or more waxes having a melting point above about 70° C. to about 85° C. which may be selected from the group consisting of linear polyethylene, microcrystalline petroleum wax, carnauba wax, lignite wax, ouricouri wax, rice bran wax, castor wax, montan wax, stearone (18-pentatriacontanone), acrawax (N,N'-ethylenebisstearamide), and combinations thereof. Preferably, the first wax component comprises linear polyethylene and/or microcrystalline petroleum wax.

In the embodiment where the ETPEA polymer has a sol-gel transition temperature $T_{gel}$ of about 70° C. to about 85° C., the second wax component has a melting point comparable to, equal to, or below about 70° C. to about 85° C. and comprises one or more waxes selected from the group consisting of bayberry wax, castor wax, Japan wax, ozokerite wax, beeswax, candelilla wax, petrolatum, ceresin wax, cocoa butter, illipe butter, esparto wax, ethylene glycol diesters or triesters of $C_{18}$-$C_{36}$ fatty acids, cetyl palmitate, paraffin wax, hard tallow, lanolin, lanolin alcohol, cetyl alcohol, glyceryl monostearate, sugarcane wax, jojoba wax, stearyl alcohol, silicone waxes, and combinations thereof. Preferably, the second wax component comprises ozokerite wax.

In one embodiment, the compositions do not comprise carnauba wax. In another embodiment, the compositions do not comprise candelilla wax.

In a preferred embodiment according to the invention, the composition will comprise ozokerite wax and at least one, or at least two, other waxes. Preferably, at least one of the additional waxes will have a melting point greater than that of the ozokerite wax, and preferably at least two additional waxes will have a melting point above ozokerite. In another embodiment, the composition will comprise ozokerite wax and at least one, or at least two, other waxes, with the proviso that at least one of the additional waxes, preferably at least two of the additional waxes, are synthetic waxes. In yet another embodiment of the invention, the compositions will comprise ozokerite wax and at least, preferably at least two, additional waxes selected from microcrystalline petroleum wax and polyolefin wax, including without limitation linear polyethylene wax.

An exemplary composition according to the invention comprises the ETPEA gellant Bis-Stearyl Ethylenediamine/Neopentyl Glycol/Stearyl Hydrogenated Dimer Dilinoleate copolymer and the first wax component comprises or consists essentially of microcrystalline petroleum wax and/or linear polyethylene wax and the second wax component comprises or consists essentially of ozokerite wax. In this context, the phrase "consists essentially of" is intended to exclude any additional wax components, the presence of which would adversely impact one or more of gloss, hardness, and/or rheology as compared to the same composition without the additional wax(es).

The first and second wax components each are present in the formulation from about 0.15 to about 20% by weight based on the total weight of the formulation. Preferably, each wax component comprises from about 0.5 to about 15% by weight of the total composition. In one embodiment, the first and second wax components collectively comprise from about 1 to about 12% by weight or from about 1 to less than 12% by weight, both of which represent wax levels below the levels conventionally used in lipsticks. In other embodiments, the first wax component comprises from about 1, 5, or about 10% to about 12 or about 15% by weight and the second wax component comprises from about 0.1, 0.5, 1, or about 5% to about 5, 10, or about 12% by weight of the total composition. It will be understood the first wax component includes all waxes in the composition having melting points above the sol-gel transition temperature $T_{gel}$ of the ETPEA polymer and, likewise, the second wax component comprises all waxes in the composition having a melting point comparable to, equal to, or below $T_{gel}$ of the ETPEA polymer.

In one embodiment according to the invention, the composition will comprise from about 0.1 to about 5%, typically from 0.5 to about 3%, more typically from about 0.5 to about 2.5%, and preferably from about 1 to about 2% ozokerite wax and at least one, or at least two, other waxes whose combined weight typically ranges from about 2.5 to about 15%, more typically from about 3% to about 12%, preferably from about 4% to about 10%, and more preferred still from about 5% to about 8% by weight. In one embodiment, ozokerite wax will comprise from about 1 to about 2% by weight of the composition and at least one, preferably at least two, additional waxes selected from microcrystalline petroleum wax and polyolefin wax, including without limitation linear polyethylene wax, will comprise from about 5% to about 8% by weight of the total composition.

Typically, the wax component having a melting point comparable to, equal to, or below the sol-gel transition temperature $T_{gel}$ of ETPEA polymer (i.e., the low melting point wax component) will be present in a weight ratio to the ETPEA polymer from about 20:1 to about 1:20, more typically from about 10:1 to about 1:10, and usually from about 5:1, 4:1, 3:1 or 2:1 to about 1:2, 1:3, 1:4 or 1:5. In some embodiments, the low melting point wax component will equal or exceed, on a weight basis, the amount of ETPEA polymer such the weight ratio of the low melting point wax, preferably ozokerite, to ETPEA polymer will be greater than 1:1, preferably greater than 1.2:1, or greater than 1.4:1, or greater than 1.6:1, or greater than greater than 1.8:1, or greater than 2:1.

Typically, wax component having melting point above $T_{gel}$ of ETPEA polymer (i.e., the high melting point wax component) will be present in a weight ratio to the ETPEA polymer from about 50:1 to about 1:20, more typically from about 25:1 to about 1:10, and usually from about 15:1, 12:1, 10:1 or 8:1 to about 1:1. In some embodiments, the high melting point wax component will equal or exceed, on a weight basis, the amount of ETPEA polymer such the weight ratio of the high melting point wax component to ETPEA polymer will be greater than 1:1, preferably greater than 2:1, or greater than 4:1, or greater than 6:1, or greater than greater than 8:1, or greater than 10:1.

In some embodiments, the amount of high melting point wax component will exceed the amount low melting point wax component in the composition such that the weight ratio of the high melting point wax component to the low melting point wax component is from about 1:1 or greater to about 20:1, typically about 1.5:1 to about 15:1, more typically from about 2:1 to about 3:1, 4:1, 5:1 or 10:1.

Silicone T-Resin

While not strictly necessary to the practice of the invention, it has been surprisingly found that the incorporation of a silicone resin having tertiary connectivity of siloxy units (i.e., a T-resin) as a co-gellant provides a marked improvement in gloss, slip, and feel of cosmetic products according to the invention. Therefore, preferred embodiments will comprise a silicone T-resin, typically between about 0.1 and about 25% by weight of the entire composition.

Suitable silicone T-resins comprise alkyl and/or aryl siloxy groups, but preferably include aryl siloxy groups such as phenyl siloxy groups, in order to increase the refractive index of the resin. An example of such a resin is methyl phenyl silsesquioxane or polyphenyl silsesquioxane. Other suitable silicone T-resins include, without limitation, the $C_{2-20}$ alkyl phenyl silsesquioxane resins described in U.S. Patent Pub. No. 2004/0180011, the disclosure of which is hereby incorporated by reference. Generally, the disclosed $C_{2-20}$ alkyl phenyl silsesquioxane resins comprise the following siloxy moieties:

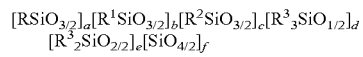
$$[RSiO_{3/2}]_a[R^1SiO_{3/2}]_b[R^2SiO_{3/2}]_c[R^3{}_3SiO_{1/2}]_d$$
$$[R^3{}_2SiO_{2/2}]_e[SiO_{4/2}]_f$$

where R is methyl; $R^1$ is $C_{2-20}$ alkyl or $C_{5-20}$ cycloalkyl; $R^2$ is phenyl, $R^3$ is $C_{1-20}$ alkyl, $C_{5-20}$ cycloalkyl, $C_{7-14}$ aralkyl, $C_{7-14}$ alkaryl, or $C_{6-10}$ aryl; and a, b, and c are such that their respective siloxy groups together comprise at least 90 mol percent of the total of siloxy moieties, preferably b and c collectively comprise 20 to 100 mol percent of the total of siloxy moieties, and d, e, and f are such that their respective moieties together comprise less than 10 mol percent of all of siloxy moieties, and preferably, d, e, and f are zero.

In one embodiment, a, d, e, and f are zero, and $R^1$ is $C_{3-8}$ alkyl, preferably propyl. The most preferred silicone T-resins are propyl phenyl silsesquioxane resins comprise the siloxy moieties $[CH_3CH_2CH_2SiO_{3/2}]_b$ and $[C_6H_5SiO_{3/2}]_c$ where the molar ratio b:c is between about 10:1 to about 1:10, preferably between about 1:1 and about 1:5, and more preferably about 1:3. The propyl phenyl silsesquioxane resins will typically have a softening point between about 40° C. and about 50° C., preferably above 45° C., and a refractive index typically greater than about 1.4, preferably greater than about 1.5, and more preferably greater than or equal to about 1.57 when measured as a film at 25° C.

A currently preferred resin is the propyl phenyl silsesquioxane resin Wacker Belsil® SPR 45 VP, available from Wacker Chemical, (Adrian, Mich.). This polymer has a refractive index of 1.55 when measure as a liquid at 82° C. and a refractive index of 1.57 when measured as a film at 25° C. The silicone T-resin is typically provided in solvent-free from, but should be compatible with (i.e., partially solubilize) fatty ester oils, silicone oils, and/or hydrocarbons to limit syneresis of these components in the finished formulation.

In some embodiments, the silicone T-resin will comprise from about 0.5%, 1%, 2%, 3%, 4%, or 5% to about 6%, 7%, 8%, 9%, 10%, 12%, 15%, or 20% of the total composition, more typically from about 4-10% of the compositions, and in one useful embodiment, from about 5-7% of the composition.

Non Polar and Low-Polarity Oils

The cosmetic compositions of the invention will include one or more low-polarity and/or non-polar oils capable of forming a gel with the ETPEA polymer. In a preferred embodiment, suitable oils are selected from the group consisting of esters, particularly fatty acid esters; silicone oils; and hydrocarbons.

Ester oils include any non-polar or low-polarity ester, including fatty acid esters. Special mention may be made of those esters commonly used as emollients in cosmetic formulations. Such esters will typically be the etherification product of an acid of the form $R_4(COOH)_{1-2}$ with an alcohol of the form $R_5(OH)_{1-3}$ where $R_4$ and $R_5$ are each independently linear, branched, or cyclic hydrocarbon groups, optionally containing unsaturated bonds, and having from 1 to 30 carbon atoms, preferably from 2 to 30 carbon atoms, and more preferably, from 3 to 30 carbon atoms, optionally substituted with one or more functionalities including hydroxyl, oxa, oxo, and the like. Preferably, at least one of $R_4$ and $R_5$ comprises at least 10, and more preferably, at least 15, 16, 17; or 18 carbon atoms, such that the ester comprises at least one fatty chain. The esters defined above will include, without limitation, the esters of mono-acids with mono-alcohols, mono-acids with diols and triols, di-acids with mono-alcohols, and tri-acids with mono-alcohols.

Suitable fatty acid esters include, without limitation, butyl acetate, butyl isostearate, butyl oleate, butyl octyl oleate, cetyl palmitate, ceyl octanoate, cetyl laurate, cetyl lactate, cetyl isononanoate, cetyl stearate, diisostearyl fumarate, diisostearyl malate, neopentyl glycol dioctanoate, dibutyl sebacate, di-$C_{12-13}$ alkyl malate, dicetearyl dimer dilinoleate, dicetyl adipate, diisocetyl adipate, diisononyl adipate, diisopropyl dimerate, triisostearyl trilinoleate, octodecyl stearoyl stearate, hexyl laurate, hexadecyl isostearate, hexydecyl laurate, hexyldecyl octanoate, hexyldecyl oleate, hexyldecyl palmitate, hexyldecyl stearate, isononyl isononanaote, isostearyl isononate, isohexyl neopentanoate, isohexadecyl stearate, isopropyl isostearate, n-propyl myristate, isopropyl myristate, n-propyl palmitate, isopropyl palmitate, hexacosanyl palmitate, lauryl lactate, octacosanyl palmitate, propylene glycol monolaurate, triacontanyl palmitate, dotriacontanyl palmitate, tetratriacontanyl palmitate, hexacosanyl stearate, octacosanyl stearate, triacontanyl stearate, dotriacontanyl stearate, stearyl lactate, stearyl octanoate, stearyl heptanoate, stearyl stearate, tetratriacontanyl stearate, triarachidin, tributyl citrate, triisostearyl citrate, tri-$C_{12-13}$-alkyl citrate, tricaprylin, tricaprylyl citrate, tridecyl behenate, trioctyldodecyl citrate, tridecyl cocoate, tridecyl isononanoate, glyceryl monoricinoleate, 2-octyldecyl palmitate, 2-octyldodecyl myristate or lactate, di(2-ethylhexyl)succinate, tocopheryl acetate, and the like.

Other suitable esters include those wherein $R_5$ comprises a polyglycol of the form H—(O—CHR*—CHR*)$_n$— wherein R* is independently selected from hydrogen or straight chain alkyl, including methyl and ethyl, as exemplified by polyethylene glycol monolaurate.

Salicylates and benzoates are also contemplated to be useful esters in the practice of the invention. Suitable salicylates and benzoates include esters of salicylic acid or benzoic acid with an alcohol of the form $R_6OH$ where $R_6$ is a linear, branched, or cyclic hydrocarbon group, optionally containing unsaturated bonds, and having from 1 to 30 carbon atoms, preferably from 6 to 22 carbon atoms, and more preferably from 12 to 15 carbon atoms. Suitable salicylates include, for example, octyl salicylate and hexyldodecyl salicylate, and benzoate esters including $C_{12-15}$ alkyl benzoate, isostearyl benzoate, hexyldecyl benzoate, benzyl benzoate, and the like.

Other suitable esters include, without limitation, polyglyceryl diisostearate/IPDI copolymer, triisostearoyl polyglyceryl-3 dimer dilinoleate, polyglycerol esters of fatty acids, and lanolin, to name but a few.

The oil may also be a volatile or non-volatile silicone oil. Suitable silicone oils include linear or cyclic silicones such as polyalkyl- or polyarylsiloxanes, optionally comprising alkyl or alkoxy groups having from 1 to 10 carbon atoms. Representative silicone oils include, for example, caprylyl methicone, cyclomethicone, cyclopentasiloxane decamethylcyclopentasiloxane, decamethyltetrasiloxane, diphenyl dimethicone, dodecamethylcyclohexasiloxane, dodecamethylpentasiloxane, heptamethylhexyltrisiloxane, heptamethyloctyltrisiloxane, hexamethyldisiloxane, methicone, methylphenyl polysiloxane, octamethylcyclotetrasiloxane, octamethyltrisiloxane, perfluorononyl dimethicone, polydimethylsiloxanes, and combinations thereof.

The silicone oil will typically, but not necessarily, have a viscosity of between about 5 and about 3,000 centistokes (cSt), preferably between 50 and 1,000 cSt measured at 25° C.

In one embodiment, the silicone oil comprises phenyl groups, as is the case for a preferred silicone oil methylphenylpolysiloxane, INCI name diphenyl dimethicone, commercially available from Shin Etsu Chemical Co under a variety of tradenames including F-5W, KF-54 and KF-56. Diphenyl dimethicones have good organic compatibility and impart film-forming characteristics to the product. Further, the presence of phenyl groups increases the refractive index of the silicone oil, further contributing to the high gloss of product. In one embodiment, the silicone oil will have a refractive index of at least 1.3, preferably at least 1.4, more preferably at least 1.45, and more preferred still at least 1.5, when measured at 25° C. Another suitable phenyl-functionalized silicone oil has the INCI name phenyltrimethicone and is sold under the trade name "DC 556" by Dow Corning. DC 556 has a refractive index of about 1.46.

In one embodiment of the invention, the silicone oil is a fluorinated silicone, preferably a perfluorinated silicone (i.e., fluorosilicones). Fluorosilicones are advantageously both hydrophobic and oleophobic and thus advantageously contribute to a desirable slip and feel of the product. Fluorosilicones also impart long-wearing characteristics to the lip product. Fluorosilicones can be gelled with behenyl behenate and further incorporated into the ETPEA gel or can be incorporated into dimethicones, which can be further incorporated into the ETPEA gel network. The preferred fluorosilicone is a fluorinated organofunctional silicone fluid having the INCI name perfluorononyl dimethicone. Perfluorononyl dimethicone is commercially available from Pheonix Chemical under the trade name Pecosil®.

The compositions may also comprise hydrocarbon oils. Exemplary hydrocarbon oils are straight or branched chain paraffinic hydrocarbons having from 5 to 80 carbon atoms, preferably from 8 to 40 carbon atoms, and more preferably from 10 to 16 carbon atoms, including but not limited to, pentane, hexane, heptane, octane, nonane, decane, undecane, dodecane, tetradecane, tridecane, and the like. Preferred hydrocarbon oils are highly branched aliphatic hydrocarbons, including $C_{8-9}$ isoparaffins, $C_{9-11}$ isoparaffins, $C_{12}$ isoparaffin, and $C_{20-40}$ isoparaffins and the like. Special mention may be made of the isoparaffins having the INCI names isohexadecane, isoeicosane, and isododecane.

Also suitable as hydrocarbon oils are polyalphaolefins, typically having greater than 20 carbon atoms, including $C_{24-28}$ olefins, $C_{30-45}$ olefins, hydrogenated polyisobutene, hydrogenated polydecene, polybutene, mineral oil, pentahydrosqualene, squalene, squalane, and the like. The hydrocarbon oil may also comprise higher fatty alcohols, such as oleyl alcohol, octyldodecanol, and the like.

Other suitable oils include without limitation castor oil, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, avocado oil, camellia oil, macadamia nut oil, turtle oil, mink oil, soybean oil, grape seed oil, sesame oil, maize oil, rapeseed oil, sunflower oil, cottonseed oil, jojoba oil, peanut oil, olive oil, and combinations thereof.

Any one of the foregoing ester oils, silicone oils, and hydrocarbon oils are contemplated to be useful in the practice of the invention. Accordingly, in one embodiment, the compositions comprise at least one oil selected from the ester oils, silicone oils, and hydrocarbon oils described above. In another embodiment, the compositions comprise two or more oils selected from the ester oils, silicone oils, and hydrocarbon oils described above. In yet another embodiment, the compositions will comprise at least one ester, at least one silicone oil, and at least one hydrocarbon oil. Because the ester oils described herein function as emollients, it is preferred that the compositions comprise at least one ester oil, and will optionally comprise at least one additional oil selected from hydrocarbon oils, silicone oils, and combinations thereof.

The oils are preferably compatible with the ETPEA polymer such that below the sol-gel transition temperature $T_{gel}$ of the ETPEA polymer, the oils are incorporated into the gel matrix. ETPEA polymers can gel variety of oils having a range of polarities, but the preferred ETPEA polymers typically, though not necessarily, are capable of optimal gellation only with low-polarity and non-polar oils. That is to say, firm gel structures, such as those required for self-supporting solids and semi-solids capable of being formulated as lipsticks, are optimally achieved with low-polarity and non-polar oils. The presence of substantial amounts of higher polarity oils and solvents tends to weaken the gel and are therefore less preferred, particularly where the gel is to be formulated as a self-supporting stick, such as a lipstick. Of course, it is within the scope of the present invention to include polar components, although high levels of such components may not be desirable for all applications.

The ability of any given molecule to interact with any other molecule may be expressed in terms of its Hansen Solubility Parameter according to the equation:

$$\delta = (\delta_D^2 + \delta_P^2 + \delta_H^2)^{1/2}$$

where $\delta_D$ is the dispersive or "nonpolar" parameter related to van der Waals interactions, $\delta_P$ is the polar parameter, related to the ability of the molecule to form dipole-dipole interactions, and $\delta_H$ is a parameter related to the ability of the molecule to hydrogen bond. Typically, $\delta_D$ does not vary significantly between different species and therefore, as a useful approximation, can be ignored. The remaining parameters, $\delta_P$ and $\delta_H$, can be calculated based on the well-known Hildebrand parameters for any given molecule and plotted in a two-dimensional "solubility space," as described in Hansen, C. M., "Hansen Solubility Parameter, A User's Handbook," CRC Press, 1999, the disclosure of which is hereby incorporated by reference herein.

Figure 2:
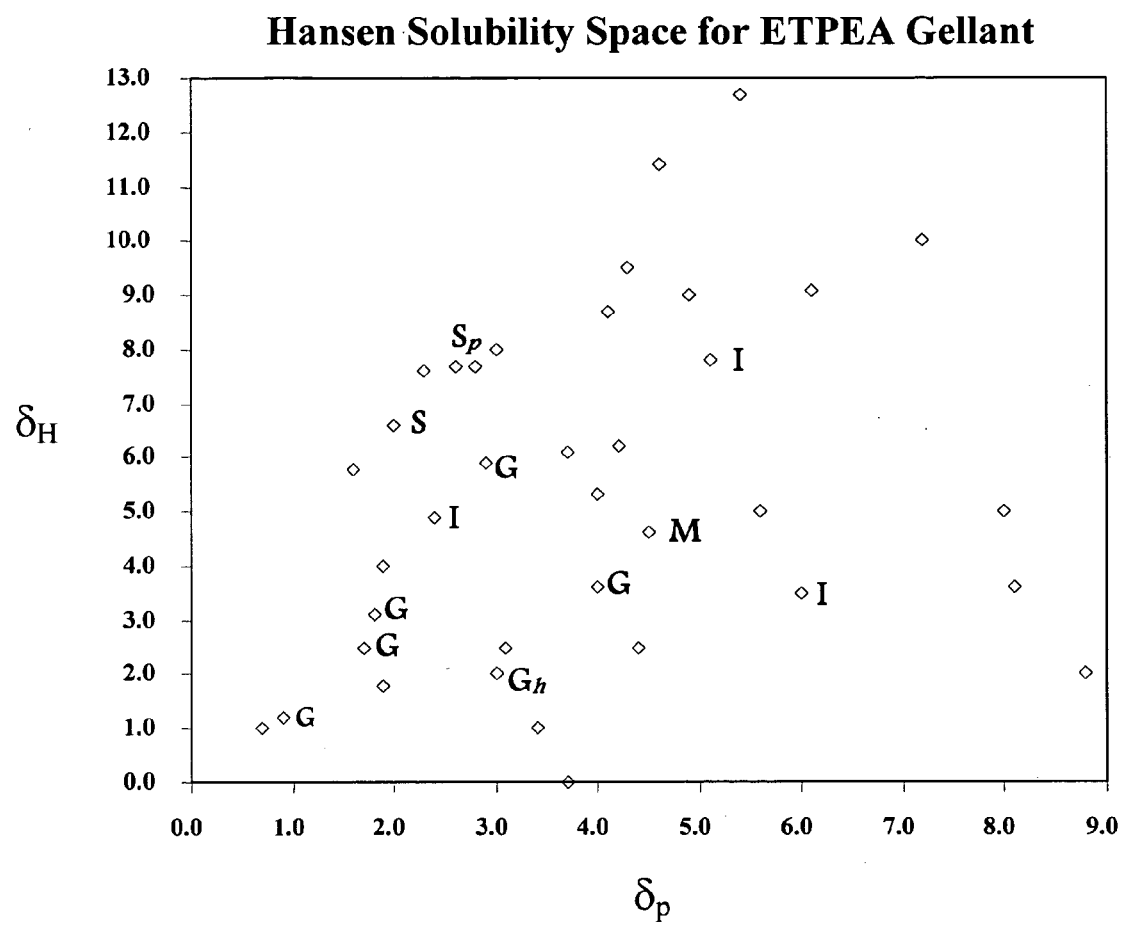
FIG. 2 shows the solubility space for an ETPEA polymeric gellant wherein each marker "◊" represents the Hansen Solubility Parameter pair ($\delta_P, \delta_H$) for various solvents and the letters represent formulations of a particular solvent with the ETPEA polymer at a polymer content of 15% by weight, where "G" is indicates a firm, clear gel; "$G_h$" indicates a firm, hazy gel; "M" indicates a cloudy, white solid; "S" indicates that the polymer was soluble in that solvent; "$S_P$" indicates that a cloudy partial solution was formed; and "I" indicates that the polymer was incompatible with the solvent.

Referring now to FIG. 2, the solvent space for the Hansen Solubility Parameters for a variety of solvents are shown. Each marker "◇" represents the parameter pair ($\delta_P, \delta_H$) for each solvent. The solvents range from relatively non-polar solvents capable of only weak hydrogen bonding interactions, such as toluene ($\delta_P=0.7$, $\delta_H=1.0$), to highly polar solvents capable of strong hydrogen bonding interactions, such as diethylene glycol ($\delta_P=7.2$, $\delta_H=10$). Also included are relatively non-polar solvents capable of significant hydrogen bonding, including 2-ethyl-1-hexanol ($\delta_P=1.6$, $\delta_H=5.8$), and highly polar solvents with weak hydrogen bonding potential, such as propylene carbonate ($\delta_P=8.8$, $\delta_H=2.0$)

The entire list of solvents shown in FIG. 2, along with the values ($\delta_p, \delta_h$) are as follows: toluene (0.7, 1.0); xylene (mixed isomers) (0.9, 1.2); 2-ethyl-1-hexanol (1.6, 5.8); methyl t-butyl ether (1.7, 2.5); n-butyl acetate (1.8, 3.1); iso-propyl palmitate (1.9, 1.8); DPMA (dipropylene glycol methyl ether acetate) (1.9, 4.0); cyclohexanol (2.0, 6.6); tripropylene glycol (2.3, 7.6); dimethyl adipate (DBE) (2.4, 4.9); DPM (dipropylene glycol methyl ether) (2.6, 7.7); n-butyl alcohol (2.8, 7.7); 2-ethylhexyl acetate (2.9, 5.9); iso-propyl alcohol (3.0, 8.0); methyl iso-butyl ketone (3.0, 2.0); cyclohexanone (3.1, 2.5); p-xylene (3.4, 1.0); ethyl lactate (3.7, 6.1); o-xylene (3.7, 0.0); diacetone alcohol (4.0, 5.3); isophorone (4.0, 3.6); hexylene glycol (2-methyl-2,2-pentanediol) (4.1, 8.7); hexanol (2-methyl-1-pentanol) (4.2, 6.2); ethyl alcohol (4.3, 9.5); methyl ethyl ketone (4.4, 2.5); EEP (ethyl-3-ethoxypropionate) (4.5, 4.6); PG (propylene glycol) (4.6, 11.4); dipropylene glycol (DPG) (4.9, 9.0); ethylene glycol phenyl ether (EPH) (5.1, 7.8); EG (ethylene glycol) (5.4, 12.7); N,N-dimethylacetamide (5.6, 5.0); N-methyl-2-pyrrolidone (6.0, 3.5); triethylene glycol (6.1, 9.1); diethylene glycol (DEG) (7.2, 10.0); DMSO (8.0, 5.0); gamma-butyrolactone (8.1, 3.6); and propylene carbonate (8.8, 2.0). While the foregoing solvents adequately envelope the optimal solubility space for the preferred ETPEA polymers of the invention, other useful ETPEA polymers may have gellation characteristics with solvents of different polarities (i.e., with polar and highly polar molecules). It is within the skill in the art to develop the solubility space over a range of polarities different from those provided herein using values of $\delta_p$ and $\delta_h$ which are readily available in the literature for a variety of solvents or are readily calculated for any given molecule based on the Hildebrand parameters.

Along with the data points ($\delta_p, \delta_h$) for the various solvents listed above, FIG. 2 also shows the experimental results of combining the ETPEA polymer SYLVACLEAR® C75V with a representative number of solvents at a 15% solids levels. The letter "G" is indicated by the tested solvents which provided a firm, clear gel, the symbol "$G_h$" indicates that a firm gel was formed, but that the gel was hazy. The letter "M" indicates that a cloudy, white solid was formed. The letter "S" indicates that the polymer was soluble in that solvent at the 15% by weight level, and the symbol "$S_p$" indicates that a cloudy partial solution was formed. The letter "I" indicates that the polymer was incompatible with the solvent. By overlaying the gellation characteristics of the ETPEA polymer with the Hansen Solubility solvent space in this manner, the range of $\delta_p$ and $\delta_h$ values required for optimal gellation may be visualized and extended to any other solvent in accordance with the fundamental principle of solubility/compatibility that "like dissolves like." For example, it may be concluded that solvents, oils, and the like having a $\delta_p$ above about 5 tend to be incompatible with the particular ETPEA polymer SYL- VACLEAR® C75V because N-methyl-2-pyrrolidone ($\delta_P$=6.0) and ethylene glycol phenyl ether (EPH) ($\delta_P$=5.1) are each incompatible with the polymer, whereas all solvents in the range of $\delta_P$=0 to 4.0 and $\delta_H$=0 to 4.0 formed gels at a level of 15% solids.

Thus, in one embodiment of the invention, the at least one ester oil, hydrocarbon oil, and/or silicone oil (or any additional solvents) will preferably have a $\delta_p$ value below about 6, i.e., from 0 to about 6. In other embodiments the ester oils, hydrocarbon oils, and/or silicone oils will have a $\delta_p$ value less than or equal to about 5, or less than or equal to about 4.5, or less than or equal to about 4, or less than or equal to about 3.5. In other embodiments, the $\delta_p$ value of the ester oils, hydrocarbon oils, and/or silicone oils will be less than or equal to about 3, 2.5, or about 1. With regard to ester oils, $\delta_p$ is typically between 0 and about 4 (i.e., less than about 4), more typically between about 0.5 and about 3, and, in some embodiments, will be between about 1 and about 2.

The hydrogen bonding parameter $\delta_h$ of the at least one ester oil, hydrocarbon oil, and/or silicone oil (or any additional solvents) will typically be below about 10, that is, between 0 and about 10. In other embodiments, $\delta_h$ will be between 0 and about 9, between 0 and about 8, between 0 and about 7, between 0 and about 6. With regard to ester oils, $\delta_H$ is typically between 0 and about 5, more typically between about 0.5 and about 4, and, in some embodiments, $\delta_H$ will be between about 1 and about 2 or 3.

In other embodiments, the ester oil, hydrocarbon oil, and/or silicone oil (or any additional solvents) will typically have a $\delta_p$ value between 0 and about 6 and a $\epsilon_h$ value between 0 and about 10. More typically, the ester oils, hydrocarbon oils, and/or silicone oils will have a $\delta_p$ value between 0 and about 5 and a $\delta_h$ value between 0 and about 8 or about 9. More preferred ester oils, hydrocarbon oils, and/or silicone oils will have a $\delta_p$ value between 0 and about 3, 3.5, 4 or about 4.5 and a $\delta_h$ value between 0 and about 4, 5, 6 or about 7.

It should be understood, however, that the invention is not limited to the use of oils having any particular solubility parameters provided that the oil is compatible with the polymer such that syneresis is limited. Thus, for example, a high polarity oil or solvent may be present in small quantities even though at higher quantities it is not capable of forming a gel with the ETPEA polymer. Preferably, oils and solvents which are incompatible with the ETPEA polymer are present at less than about 10% by weight of the composition, preferably less than about 5% of the composition, and more preferably, less than about 2.5% of the composition. Thus, in one embodiment, the inventive compositions will be substantially free of polar solvents, such as those having a $\delta_p$ value greater than about 6, greater than about 7, or greater than about 8, by which is meant that the compositions will have less than about 1% by weight of such solvents. Further, as shown in FIG. 2, some solvents solubilize the polymer at 15% by weight as indicated by the symbols "S" and "$S_p$". This does not mean that such solvents are not useful in the practice of the invention, but rather that more ETPEA polymer may be required in the formulation in order to form a suitable gel network. While the preferred compositions will typically comprise 15% ETPEA polymer or less, other embodiments will have, for example, up to about 20%, 25%, 30%, 35%, or even about 40% by weight ETPEA polymer and therefore may provide suitable gels with such solvents. Accordingly, the values of $\delta_p$ and $\delta_h$ described herein are particularly appropriate for the preferred compositions which will comprise between about 0.1 and about 15% by weight of ETPEA polymer.

The oil components will typically comprise, individually or collectively, from about 0.1% to about 90% by weight of the composition. More typically, the collective weight of all oil components (ester oils, hydrocarbon oils, and silicone oils) will constitute from about 5%, 10%, 15%, 20%, 25%, or 30% to about 65%, 70%, 75% or 80% of the total weight of the composition. In one exemplary embodiment, the oils collectively comprise between about 30% and about 70%, preferably between about 40% and about 60% by weight, of the total composition, particularly where the ETPEA polymer comprises between about 0.5 and about 12% by weight of the total composition. Excellent results have been obtained wherein the collective content of ester oils is from about 30-60% by weight, or about 40-50% by weight.

The compositions of the invention will optionally comprise one or more colorants, including pigments, dyes, lakes, and the like. As used herein, the term "pigment" is intended to include white pigments such as titanium dioxide, zinc oxide, mica, pearls, and the like. The collective weight of all colorants, when present, will usually range from about 0.1% up to about 30% of the composition, typically from about 1% to about 20%, preferably from about 2.5 to about 15%, and, in a preferred embodiment, from about 5 to about 10%. It has surprisingly been found that high levels of pigments, particularly mica and pearls, do not significantly diminish the gloss of the lip products according to the invention. In some embodiments of the invention, the 85 degree gloss value of the lip products, in the presence of between about 0.1-15%, 1-10%, 2-10%, 4-10%, 6-10%, or 8-10% by weight pearl and/or mica components, will be within 20%, preferably within 15%, more preferably within 10%, and more preferred still, within 5% of the 85 degree gloss value of an otherwise identical composition containing no pearl and/or mica components. The 85 degree gloss value will in some embodiments, be at least 45, at least 50, at least 55, or at least 60. More typically, the 85 degree gloss will be at least 65, and preferably at least 70, even in the presence of pearl and/or mica components, including for example from at least 1%, at least 2%, at least 4%, at least 6%, at least 8%, or even at least 10% by weight pearl and/or mica components. Preferred lipsticks will exhibit an 85 degree gloss value of 75 or higher, and preferably 80 or higher, across a pearl and mica loading range of 0-15% by weight.

The compositions may also comprise one or more particulates, including without limitation mica, talc, bismuth oxychloride, bentonite, nylon, silica, acrylates copolymer, teflon, spherical silica, and the like. It is believed that similar results will be obtained with any particulate material. That is to say, the gloss of the inventive compositions will not be substantially diminished by particulate levels in the range of 0-10% by weight. In this context "substantially diminished" is intended to mean that the attenuation of gloss will be less than about 20%, preferably less than 15%, more preferably less than 10%, and more preferred still, less than 5% of the 85 degree gloss value of an otherwise identical composition in the absence of the particulate material and will preferably be at least 75 or higher, and preferably 80 or higher.

In one preferred aspect of the invention, the compositions are capable of delivering high gloss when applied to the lips. By the term "high gloss" is meant an 85 degree gloss value greater than about 70, typically greater than about 75, and preferably greater than about 80. It has surprisingly been found that lipstick products prepared with the inventive compositions can exhibit a gloss comparable to or even greater than conventional wax-free oil-based lip gloss products. Thus, in some embodiments, the 85 degree gloss value of a lipstick comprising the inventive compositions will be greater than about 82, 84, 86, 88, or even 90. It is contemplated that 85 degree gloss values of 95 or even higher may be achieved by the inventive lip products.

In embodiments where the compositions are to be formulated as a self-supporting stick, the compositions will have a hardness above 40 g (grams). Typically, the compositions will have a hardness above about 50 g and more typically above about 60 g. Preferably, the compositions will have a hardness above about 70 g, 80 g, 90 g or 100 g. In some embodiments, the hardness of the compositions will be at least 120 g, 140 g, 160 g, 180 g, or 200 g. In other embodiments, the compositions will have a hardness of at least 250 g, 300 g, 350 g, or 400 g. However, in the broadest aspects, the invention is not strictly limited to compositions having any particular hardness. The compositions are contemplated to be useful even when provided as weak gels and the like. Surprisingly, it has been found that even relatively hard sticks, for example those having a hardness between about 200 g and about 300 g, exhibit excellent "pay off" such that upon application to the lips an acceptable amount of product is transferred to the lips. The assessment of pay off is well-known in the art and may be quantified, for example, by expert panel testing on a scale from 1 to 10, etc.

In one aspect, the inventive compositions provide a unique rheology not obtainable with conventional wax-based lipsticks. The rheology is characterized by a perception that the lipstick retains a freshly applied feeling on the lips over a long period of wear, meaning that the feeling of the lipstick remains unctuous over that time. Conventional wax-based lipsticks are known to initially feel oily when applied but rapidly become dry, particularly after the wearer rubs their lips together and the like. This effect is believed to arise due to the breakdown of the wax structure brought about by shear from rubbing the lips, etc. This effect may be described as the shear-induced breakdown of the wax matrix.

In contrast to conventional lipsticks, the compositions of the invention do not exhibit shear-induced breakdown of the gel structure, or exhibit reduced shear-induced breakdown of the gel structure as compared to wax-based lipsticks. The result is that the lipsticks of the invention retain a long wearing oily feeling on the lips. This effect may by quantified in terms of the viscosity of the composition over repeated shear cycles. Typically, the inventive compositions have rheology characterized by a viscosity at a given shear rate which remains substantially constant over repeated shear cycles, particularly with shear rates between about 1 and about 10 $sec^{-1}$ typically encountered during wear. That is to say, the gel network remains elastic such that shear does not induce degradation of the network. In contrast, the wax base of conventional lipsticks undergoes shear induced degradation such that the viscosity of the wax decreases with repeated shear cycles. By "relatively constant" is mean that, while some variance in the viscosity/shear rates profiles is tolerable over multiple shear cycles, the second shear cycle should produce a viscosity falling within ±3 SD (standard deviation) of the viscosity measured in a first shear cycle at each shear rate between about 1 and about 10 $sec^{-1}$. Preferably, the viscosity measured in a second shear cycle will be within ±2 SD, more preferably ±1 SD of the viscosity measured in a first shear cycle at each shear rate between about 1 and about 10 $sec^{-1}$.

In some embodiments, the viscosity during a second and third shear cycle will be within ±3 SD, ±2 SD, or ±1 SD of the viscosity measured in a first shear cycle at each shear rate between about 1 and about 10 $sec^{-1}$.

In some embodiments, the viscosity of the inventive compositions during a second shear cycle, and preferably during a third shear cycle, will be greater than about 50, 75, or about 100 Pa·sec at every shear rate between about 1 and about 5 $sec^{-1}$ and/or the viscosity during a second shear cycle, and preferably during a third shear cycle, will be greater than about 5, 7.5 or about 10 Pa·sec at every shear rate between about 10 and about 50 $sec^{-1}$ and/or the viscosity of the inventive compositions during a second shear cycle, and preferably during a third shear cycle, will be greater than about 0.5, 0.75, or about 1 Pa·sec at shear rates between about 100 and about 500 $sec^{-1}$ wherein said second shear cycles follows a first shear cycle covering shear rates from about 1 to about 1,000 $sec^{-1}$.

In one embodiment, the composition for imparting an unctuous film to the lips comprises:
 (a) from about 0.1 to about 40% by weight of an ester terminated poly(ester-amide) polymer having an average molecular weight between about 3,000 and about 7,500 Daltons and being capable of forming a gel with low-polarity and nonpolar oils at or below a sol-gel transition temperature $T_{gel}$ wherein $T_{gel}$ is above body temperature;
 (b) from about 0.1 to about 20% by weight of a first wax component comprising one or more waxes having a melting point above $T_{gel}$;
 (c) from about 0.1 to about 20% by weight of a second wax component comprising one or more waxes having a melting point at or below $T_{gel}$; and
 (e) one or more low-polarity or nonpolar oils capable of forming a gel with said ester terminated poly(ester-amide) polymer at or below said sol-gel transition temperature $T_{gel}$; wherein said one or more low-polarity or nonpolar oils are selected from the group consisting of esters, hydrocarbons, and silicone-based oils;
wherein the composition is characterized by a viscosity measured during a second shear cycle that is within ±20% of the viscosity measured during a first shear cycle at every shear rate between about 1 and about –10 $sec^{-1}$, wherein the first and the second shear cycles are identical and comprise increasing shear rates from about 1 to about 1,000 $sec^{-1}$.

In one variant, the second shear cycle is within ±10% of the viscosity measured during the first shear cycle at every shear rate between about 1 and about 10 $sec^{-1}$. In another variant, the viscosity measured during the second shear cycle is within ±5% of the viscosity measured during the first shear cycle at every shear rate between about 1 and about 10 $sec^{-1}$.

In another embodiment, the compositions are characterized by a viscosity measured during the second shear cycle that is within ±20% of the viscosity measured during the first shear cycle at every shear rate between about 10 and about 100 $sec^{-1}$. In one variant according to this embodiment, the viscosity measure during the second shear cycle is within ±10% of the viscosity measured during the first shear cycle at every shear rate between about 10 and about 100 $sec^{-1}$. In another variant, the viscosity measured during the second shear cycle is within ±5% of the viscosity measured during the first shear cycle at every shear rate between about 10 and about 100 $sec^{-1}$.

In yet another embodiment, the viscosity measured during the second shear cycle is within ±20% of the viscosity measured during the first shear cycle at every shear rate between about 1 and about 100 $sec^{-1}$. In one variant according to this embodiment, the viscosity measured during the second shear cycle is within ±10% of the viscosity measured during the first shear cycle at every shear rate between about 1 and about 100 $sec^{-1}$. Preferably, the viscosity measured during the second shear cycle is within ±5% of the viscosity measured during the first shear cycle at every shear rate between about 1 and about 100 $sec^{-1}$.

The compositions for imparting an unctuous film to the lips may be further characterized by a viscosity greater than about 50, 75, or about 100 Pa·sec at a shear rate of about 1 sec$^{-1}$ as measured during a first shear cycle. Preferably, the compositions are characterized by a viscosity greater than about 50, 75, or about 100 Pa·sec at a shear rate of about 1 sec$^{-1}$ as measured during both the first and second shear cycles. In one variant, the compositions are characterized by a viscosity greater than about 50, 75, or about 100 Pa·sec at shear rates from about 1 to about 5 sec$^{-1}$ as measured during the first shear cycle, and preferably during the first and second shear cycles.

Preferred compositions will be characterized by a viscosity greater than about 5, 7.5, or about 10 Pa sec at a shear rate of about 10 sec–1 as measured during said first shear cycle and preferably will have a viscosity greater than about 5, 7.5, or about 10 Pa·sec at a shear rate of about 10 sec–1 as measured during the first and second shear cycles. More preferred compositions will be characterized by a viscosity greater than about 5, 7.5, or about 10 Pa·sec at a shear rate from about 10 to about 50 sec–1 as measured during the first shear cycle, and preferably as measured during both the first and second shear cycles.

In other embodiments, the compositions will further be characterized by a viscosity greater than about 0.5, 0.75, or about 1 Pa·sec at a shear rate of about 100 sec$^{-1}$ as measured during said first shear cycle and preferably will have a viscosity greater than about 0.5, 0.75, or about 1 Pa·sec at a shear rate of about 100 sec$^{-1}$ as measured during the first and the second shear cycles.

Alternatively, the rheology may be quantified by expert panel testing on a 0-10 scale on the basis of parameters such as slip, feel, oiliness, moisture, and/or dryness over a period of wear, including for example 15 minutes, 30 minutes, 45 minutes, and 1 hour.

It will be understood that the selection of and amounts of ETPEA polymer, wax, oil, silicone T-resin, etc., described herein are equally applicable to both the compositions for imparting high gloss and compositions having the improved rheology described herein. In preferred aspects of the invention, the lip compositions will exhibit both high gloss and improved rheology.

The compositions of the invention may further comprise one or more film formers and polymers. Fluorinated polymers, such as those having the INCI name polyperfluoromethylisopropyl ether, are particularly useful to modify slip and feel of the composition. Preferred fluorinated polymers are supplied by Solvey Solexis under the trade name FOMBLIN HC. Sucrose acetate isobutyrate (INCI) supplied by Eastman Chemical and glycerol rosinate (INCI) sold under the trade name SylvaGum RE 85K by Arizona Chemical are preferred film formers.

Various fillers may be incorporated into the compositions. Suitable fillers include without limitation silica, treated silica, talc, zinc stearate, mica, kaolin, Nylon powders such as Orgasol™, polyethylene powder, Teflon™, starch, boron nitride, copolymer microspheres such as Expancel™ (Nobel Industries), Polytrap™ (Dow Corning) and silicone resin microbeads (Tospearl™ from Toshiba), and the like.

Additional pigment/powder fillers include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide. Other useful powders are disclosed in U.S. Pat. No. 5,688,831, the disclosure of which is hereby incorporated by reference.

The compositions of the invention will typically comprise one or more coloring agents. Suitable coloring agents, including pigments, lakes, and dyes, are well known in the art and are disclosed in the C.T.F.A. Cosmetic Ingredient Handbook, First Edition, 1988, the contents or which are hereby incorporated by reference. Organic pigments include, for example, FD&C dyes, D&C dyes, including D&C Red, Nos. 2, 5, 6, 7, 10, 11, 12, 13, 30 and 34, D&C Yellow No. 5, Blue No. 1, Violet No. 2. Exemplary inorganic pigments include, but are not limited to, metal oxides and metal hydroxides such as magnesium oxide, magnesium hydroxide, calcium oxide, calcium hydroxides, aluminum oxide, aluminum hydroxide, iron oxides ($\alpha$-Fe$_2$O$_3$, y-Fe$_2$O$_3$, Fe$_3$O$_4$, FeO), red iron oxide, yellow iron oxide, black iron oxide, iron hydroxides, titanium dioxide, titanium lower oxides, zirconium oxides, chromium oxides, chromium hydroxides, manganese oxides, cobalt oxides, cerium oxides, nickel oxides and zinc oxides and composite oxides and composite hydroxides such as iron titanate, cobalt titanate and cobalt aluminate. Other suitable colorants include ultramarine blue (i.e., sodium aluminum silicate containing sulfur), Prussian blue, manganese violet, bismuth oxychloride, talc, mica, sericite, magnesium carbonate, calcium carbonate, magnesium silicate, aluminum magnesium silicate, silica, titanated mica, iron oxide titanated mica, bismuth oxychloride, and the like. The colorants may be surface modified with, for example, fluoropolymers, to adjust one or more characteristics of the colorant as described in, for example, U.S. Pat. Nos. 6,471,950, 5,482,547, and 4,832,944, the contents of which are hereby incorporated by reference. Suitable pearling pigments include without limitation bismuth oxychloride, guanine and titanium composite materials containing, as a titanium component, titanium dioxide, titanium lower oxides or titanium oxynitride, as disclosed in U.S. Pat. No. 5,340,569, the contents of which are hereby incorporated by reference. The composition may also contain a cosmetically acceptable glitter, including metallic particles or solid organic particles such as those described in U.S. Patent Pub. 2002/0006422, the contents of which are hereby incorporated by reference.

The compositions of the invention may further comprise a cosmetic vehicle, including without limitation linear and cyclic volatile silicones, including those available from the Dow Corning Corporation under the tradenames Dow Corning 244, 245, 344, and 200 fluids. These fluids include octamethylcyclotetrasiloxane, decamethylcyclopentasiloxane, hexamethyldisiloxane, or mixtures thereof. Also contemplated to be useful are the branched volatile silicones commercially available from Shinetsu. Water soluble vehicles such as butylene glycol, propylene glycol, polyglycerol diisostearate, dimethylsiloxane/glycol copolymer, isopropyl myristate, triisostearyl citrate, and the like may also be present. The weight percentage of the vehicle, excluding ester oils, silicone oils, and hydrocarbon oils capable of forming a gel with the ETPEA polymer, will typically be less than about 10% by weight, more typically less than about 5% by weight, and preferably less than about 1% by weight of the composition.

The compositions of the invention may optionally comprise other active and inactive ingredients typically associated with cosmetic and personal care products, including, but not limited to, excipients, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, antiallergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfolients, lubricants, fragrances, colorants, staining agents, depigmenting agents, hypopigmenting agents, preservatives, stabilizers, pharmaceutical agents, photostabilizing agents, and mixtures thereof. In addition to the foregoing, the compositions of the invention may contain any other compound for the treatment of skin disorders.

Example I

High Gloss Lipstick

Table 2 provides a high gloss lipstick comprising the ETPEA gellant Sylvaclear® C75V (Arizona Chemicals), a high melting point wax component (microcrystalline petroleum wax and linear polyethylene), a low melting point wax component (ozokerite), a high refractive index silicone T-resin co-gellant, and a variety of low-polarity ester oils.

TABLE 2

| Component | Function | Weight % |
| --- | --- | --- |
| Microcrystalline Petroleum Wax | First wax component | 0.6 |
| Polyethylene-Linear Pl | First wax component | 5.85 |
| Ozokerite 170-D | Second wax component | 1.55 |
| Sylvaclear ® C75V | ETPEA gellant | 1.0 |
| Polyphenylsilsesquioxane | Silicone T-resin gellant | 5.9 |
| Silica-High Oil Absorbing | Particulate based gelling agent | 2.0 |
| Triisostearoyl Polyglyceryl-3 Dimer Dilinoleate | Esters | 9.0 |
| Diisopropyl Dimerate | Esters | 2.5 |
| Triisostearyl Trilinoleate | Esters | 13.6 |
| C12-15 Alcohols Benzoate | Esters | 2.0 |
| Octyldodecyl Stearoyl Stearate | Esters | 6.15 |
| Diisostearyl Fumarate | Esters | 15.5 |
| Polyglyceryl-2 Diisostearate/IPDI Copolymer | Esters | 3.5 |
| Sucrose Acetate Isobutyrate | Film former | 2.5 |
| VP/Eicosene Copolymer | Film former | 1.65 |
| PVP/Hexadecene Copolymer | Film former | 4.0 |
| Lanolin-Low Odor | Film former | 6.5 |
| Glyceryl Rosinate-Food Grade | Film former | 0.5 |
| Ethylhexyl-Methoxycinnamate | Sunscreen | 7.0 |
| Octocrylene | Sunscreen | 2.0 |
| Caprylyl Glycol | Preservative | 0.5 |
| Sucralose | Sweetener | 0.02 |
| Colorants | Colorants | 6.03 |
| Fragrance | Fragrance | 0.15 |

The product was prepared by mixing the ingredients of Table 2 above 100° until all of the waxy components melted. The molten mixture was poured into a mold and allowed to solidify. The resulting product was a self-supporting solid having physical stiffness comparable to a conventional lip stick.

A glossmeter was used to measure the specular reflection from a film of the lipstick at 85 degrees. The average of multiple measurements was 87 which far exceeds the gloss of conventional wax-based lipsticks and, surprisingly exceeds the gloss of some liquid lip gloss products and two-coat high gloss lip products. FIG. 1 compares the 85 degree gloss of the lipstick of Table 2 with the several conventional lip products. In FIG. 1, "A" represents the lipstick of Table 2, and the remaining lip products are as follows: B=Glazewear™ liquid lip gloss (Avon Products); C=Color Rich™ (shade 1) (Avon Products); D=Color Rich™ (shade 2) (Avon Products); E=Butter Shine™ (Clinique); F=Ultra Color Rich™ (shade 1) (Avon Products); G=Ultra Color Rich™ (Shade 2) (Avon Products); H=Moisture Extreme™ (Maybelline); I=Shine Supreme™ (Avon Products); J=Colour Riche™ (L'Oreal); K=Wet Shine™ (shade 1) (Maybelline); L=Wet Shine™ (shade 2) (Maybelline); M=Brilliant Moisture™ (shade 1) (Avon Products); N=Brilliant Moisture™ (shade 2) (Avon Products); and O represents a two-step lip product of the type involving a transparent, high gloss top coat.

Notably, the 85 degree gloss value of the lipstick of Table 2 outperforms not only the conventional wax-based lipsticks (C-N), but also the liquid lip gloss (B) and the two step lip product (O), which heretofore represented the state of the art in delivering high shine.

Example II

The effect of increasing pearl and mica content on the 85 degree gloss of lip products was investigated. Four samples of the inventive lipsticks having pearl and mica contents ranging from 0% to 10% by weight were prepared. The formulations for the four samples are provided in Table 3.

TABLE 3

| Weight % | Weight % | Weight % | Weight % | Component |
| --- | --- | --- | --- | --- |
| 0.6 | 0.6 | 0.6 | 0.6 | Microcrystalline Petroleum Wax |
| 5.85 | 5.85 | 5.85 | 5.85 | Polyethylene-Linear Pl |
| 1.55 | 1.55 | 1.55 | 1.55 | Ozokerite 170-D |
| 1.0 | 1.0 | 1.0 | 1.0 | Sylvaclear ® C75V |
| 5.9 | 5.9 | 5.9 | 5.9 | Polyphenylsilsesquioxane |
| 2.0 | 2 | 1.5 | 2.0 | Silica-High Oil Absorbing |
| 9.0 | 9.0 | 9.0 | 9.0 | Triisostearoyl Polyglyceryl-3 Dimer Dilinoleate |
| 2.5 | 2.5 | 2.5 | 2.5 | Diisopropyl Dimerate |
| 13.6 | 13.6 | 13.6 | 9.38 | Triisostearyl Trilinoleate |
| 2.0 | 2.0 | 2.0 | 2.0 | C12-15 Alcohols Benzoate |
| 6.15 | 6.15 | 6.15 | 6.15 | Octyldodecyl Stearoyl Stearate |
| 15.5 | 15.5 | 17 | 10.5 | Diisostearyl Fumarate |
| 3.5 | 3.5 | 3.0 | 3.5 | Polyglyceryl-2 Diisostearate/IPDI Copolymer |
| 2.5 | 2.5 | 2.0 | 2.5 | Sucrose Acetate Isobutyrate |
| 1.65 | 1.65 | 1.65 | 1.65 | VP/Eicosene Copolymer |
| 4.0 | 4.0 | 4.0 | 4.0 | PVP/Hexadecene Copolymer |
| 6.5 | 6.5 | 6.5 | 6.5 | Lanolin-Low Odor |
| 0.5 | 0.5 | 0.5 | 0.5 | Glyceryl Rosinate-Food Grade |
| 7.0 | 7.0 | 7.0 | 7.0 | Ethylhexyl-Methoxycinnamate |
| 2.0 | 2.0 | 2.0 | 2.0 | Octocrylene |
| 0.5 | 0.5 | 0.5 | 0.5 | Caprylyl Glycol |
| 0.02 | 0.02 | 0.02 | 0.02 | Sucralose |
| 6.03 | 2.78 | 0.88 | 5.25 | Colorants |
| — | 3.25 | 5.15 | 10 | Pearls and Mica |
| 0.15 | 0.15 | 0.15 | 0.15 | Fragrance |

The gloss of the inventive lipsticks were compared against a conventional wax-based lipstick having pearl and mica contents ranging from 2% to about 10% by weight, as shown in Table 4.

TABLE 4

| Sample 1 | Sample 2 | Sample 3 | Sample 4 | Component |
|---|---|---|---|---|
| | | Weight % | | |
| 4.60 | 4.60 | 4.60 | 4.60 | micro wax white |
| 2.75 | 2.75 | 2.75 | 2.75 | polyethylene-linear pl |
| 5.00 | 5.00 | 5.00 | 5.00 | ozokerite 170-D |
| 12.00 | 12.00 | 12.00 | 12.00 | diglyceryl diisostearate |
| 20.00 | 20.00 | 20.00 | 20.00 | glyceryl triacetyl hydroxystearate |
| 2.00 | 2.00 | 2.00 | 2.00 | polyglycerol diisostearate |
| 16.30 | 16.30 | 16.30 | 16.30 | triisostearyl trilinoleate |
| 1.60 | 1.60 | 1.60 | 1.60 | phenyl trimethicone/bentone gel |
| 8.80 | 8.80 | 8.80 | 8.80 | hydrogenated polyisobutene |
| 8.00 | 8.00 | 8.00 | 8.00 | lanolin acetate |
| 5.50 | 5.50 | 5.50 | 5.50 | polybutene |
| 0.12 | 0.12 | 0.12 | 0.12 | acrylate copolymer E0603 |
| 1.75 | 1.75 | 1.75 | 1.75 | polyethylene 1-20 microns |
| 0.50 | 0.50 | 0.50 | 0.50 | caprylyl glycol |
| 8.96 | 7.0 | 5.08 | 0.6 | colorants |
| 2.00 | 3.96 | 5.88 | 10.36 | pearls and mica |
| 0.12 | 0.12 | 0.12 | 0.12 | fragrance |

Figure 3:
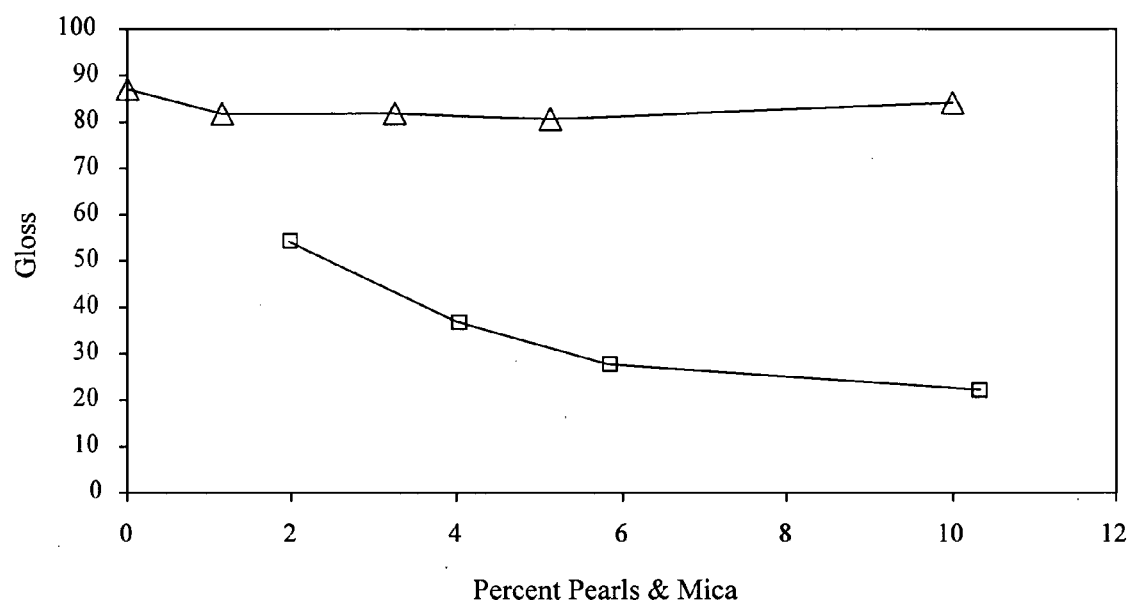
FIG. 3 compares the specular reflection at 85 degrees for and ETPEA gel-based lipstick (Δ) and a conventional wax-based lipstick (□) at the various pearl and mica loadings.

FIG. 3 compares the 85° gloss for the four ETPEA gel-based lipsticks (indicated by the data points "Δ") and the four samples of wax-based lipstick (indicated by the data points "☐") at the various pearl and mica loadings. Clearly evident is the fact that the gloss does not significantly diminish over the 0-10% by weight range for the ETPEA gel-based formulations of the invention, and in all cases remains quite high, i.e., greater than 80, whereas in the convention wax-based lipsticks the 85 degree gloss diminishes substantially (greater than about 50%) over mica and pearl loadings of 2 to about 10% by weight. The data corresponding to FIG. 3 is shown below in Table 5.

TABLE 5

| Pearl & Mica (wt. %) | 85° Gloss |
|---|---|
| gel base (Δ) | |
| 0 | 87 |
| 1.16 | 81.85 |
| 3.25 | 82 |
| 5.15 | 80.3 |
| 10 | 83.85 |
| wax base (☐) | |
| 2 | 54 |
| 3.96 | 37 |
| 5.88 | 27.5 |
| 10.36 | 22 |

Further, it is evident that the conventional wax-based formulations provide inferior gloss as compared to the inventive lipsticks over the entire range of pearl and mica loading. Thus, one surprising advantage of the compositions of the invention is that they permit the formulator to include high levels of pearling agents without sacrificing shine. By "high levels" is meant at least 5%, preferably at least 7.5%, and more preferably at least 10% or at least 12% by weight.

Example III

The formulation parameters effecting the hardness of the ETPEA gel were investigated using the various lipstick formulation shown in Table 6. The hardness of each lipstick was measured on a Texture Analyzer Model QTS-25 equipped with a 4 mm stainless steel probe (TA-24). As the data in Table 6 illustrates, the firmness of the gel is the result of a complex interaction between the ETPEA, wax, silicone T-resin, oil, and pigments/pearl contents of the lipstick. In each case, the formulations in Table 6 are expressed as weight percent of the entire formulation so that the ester oil content varies somewhat between each sample to accommodate the increase or decrease in the ETPEA, silicone T-resin, wax, and pigment/pearl components. Nevertheless, general trends are observed for the effect of varying the ETPEA, wax, silicone T-resin, oil, and pigments/pearl contents of the lipstick.

TABLE 6

| Component | Sample Number: | | | | | | | | | |
|---|---|---|---|---|---|---|---|---|---|---|
| | 1 | 2 | 3 | 4 | 5 | 6 | 7 | 8 | 9 | 10 |
| | | | | | Weight % | | | | | |
| Microcrystalline Petroleum Wax | 0.60 | 0.60 | 0.60 | 0.70 | 0.55 | 0.60 | 0.60 | 0.43 | 0.38 | 0.53 |
| Polyethylene-Linear Pl | 5.85 | 5.85 | 5.85 | 7.00 | 5.00 | 5.85 | 5.85 | 4.18 | 3.67 | 5.13 |
| Ozokerite 170-D | 1.55 | 1.55 | 1.55 | 1.90 | 1.30 | 1.55 | 1.55 | 1.11 | 0.97 | 1.36 |
| Sylvaclear ® C75V | 1.00 | 1.00 | 5.90 | 5.90 | 5.90 | 12.00 | 4.90 | 28.57 | 25.06 | 0.88 |
| Polyphenylsilsesquioxane | 5.90 | 5.90 | 5.90 | 5.90 | 5.90 | 2.00 | 2.00 | 4.21 | 15.98 | 17.54 |
| Silica-High Oil Absorbing | 2.00 | 2.00 | 2.00 | 2.00 | 2.00 | 2.00 | 2.00 | 1.43 | 1.25 | 1.75 |
| Triisostearoyl Polyglyceryl-3 Dimer Dilinoleate | 9.00 | 9.00 | 9.00 | 9.00 | 9.00 | 9.00 | 9.00 | 6.43 | 5.64 | 7.89 |
| Diisopropyl Dimerate | 2.50 | 2.50 | 2.50 | 2.50 | 2.50 | 2.50 | 2.50 | 1.79 | 1.57 | 2.19 |
| Triisostearyl Trilinoleate | 9.38 | 13.60 | 10.65 | 9.05 | 11.00 | 10.00 | 13.60 | 9.71 | 8.52 | 11.93 |
| C12–15 Alcohols Benzoate | 2.00 | 2.00 | 2.00 | 2.00 | 2.00 | 2.00 | 2.00 | 1.43 | 1.25 | 1.75 |
| Octyldodecyl Stearoyl Stearate | 6.15 | 6.15 | 6.15 | 6.15 | 6.15 | 6.15 | 6.15 | 4.39 | 3.85 | 5.39 |
| Diisostearyl Fumarate | 10.50 | 15.50 | 13.55 | 13.55 | 13.55 | 12.00 | 15.50 | 11.07 | 9.71 | 13.60 |
| Polyglyceryl-2 Diisostearate/IPDI Copolymer | 3.50 | 3.50 | 3.50 | 3.50 | 3.50 | 3.50 | 3.50 | 2.50 | 2.19 | 3.07 |
| Sucrose Acetate Isobutyrate | 2.50 | 2.50 | 2.50 | 2.50 | 2.50 | 2.50 | 2.50 | 1.79 | 1.57 | 2.19 |
| VP/Eicosene Copolymer | 1.65 | 1.65 | 1.65 | 1.65 | 1.65 | 1.65 | 1.65 | 1.18 | 1.03 | 1.45 |
| PVP/Hexadecene Copolymer | 4.00 | 4.00 | 4.00 | 4.00 | 4.00 | 4.00 | 4.00 | 2.86 | 2.51 | 3.51 |
| Lanolin-Low Odor | 6.50 | 6.50 | 6.50 | 6.50 | 6.50 | 6.50 | 6.50 | 4.64 | 4.07 | 5.70 |
| Glyceryl Rosinate-Food Grade | 0.50 | 0.50 | 0.50 | 0.50 | 0.50 | 0.50 | 0.50 | 0.36 | 0.31 | 0.44 |
| Ethylhexyl-Methoxycinnamate | 7.00 | 7.00 | 7.00 | 7.00 | 7.00 | 7.00 | 7.00 | 5.00 | 4.39 | 6.14 |
| Octocrylene | 2.00 | 2.00 | 2.00 | 2.00 | 2.00 | 2.00 | 2.00 | 1.43 | 1.25 | 1.75 |
| Caprylyl Glycol | 0.50 | 0.50 | 0.50 | 0.50 | 0.50 | 0.50 | 0.50 | 0.36 | 0.31 | 0.44 |
| Sucralose | 0.02 | 0.02 | 0.02 | 0.02 | 0.02 | 0.02 | 0.02 | 0.01 | 0.01 | 0.02 |

TABLE 6-continued

| Component | Sample Number: | | | | | | | | | |
|---|---|---|---|---|---|---|---|---|---|---|
| | 1 | 2 | 3 | 4 | 5 | 6 | 7 | 8 | 9 | 10 |
| | Weight % | | | | | | | | | |
| Pigments & Pearls | 15.25 | 6.03 | 6.03 | 6.03 | 6.03 | 6.03 | 6.03 | 4.31 | 3.78 | 5.29 |
| Fragrance | 0.15 | 0.15 | 0.15 | 0.15 | 0.15 | 0.15 | 0.15 | 0.11 | 0.09 | 0.13 |
| Hardness (grams) | 204 | 201 | 62 | 174 | 117 | 43 | 109 | 271 | 272 | 413 |
| | (±1.25) | (±5.44) | (±1.63) | (±1.25) | (±3.27) | (±2.62) | (±1.40) | (±1.41) | (±2.16) | (±5.56) |

For example, Samples 1 and 2 contain the identical amounts of wax, ETPEA polymer, and silicone T-resin, but differ primarily in the weight percentage of pigments and pearl (15.25% vs. 6.03%), however no significant loss of hardness was observed (204 g vs. 201 g).

Samples 2 and 3 contain identical weight percentages of wax, silicone T-resin, and pigments/pearls, but differ in amount of ETPA gellant from 1% (Sample 2) to 5.9% (Sample 3). The corresponding hardness is seen to decrease with increasing ETPEA polymer from 201 g at 1% to 62 g at 5.9% ETPEA. The latter hardness is only slightly above the hardness threshold (40 g) for making a suitable self-supporting stick. The loss of hardness in Sample 3 is likely the consequence of increasing the ratio of ETPEA polymer to ester oils from about 1:52 in Sample 2 to about 1:8 in Sample 3. Thus, it may be said that the preferred gels will have a weight ratio of ETPEA polymer to ester oils of less than 1:8, typically less than 1:10, preferably less than 1:15, more preferably less than 1:20, and more preferred still less than 1:30, particularly in embodiments having a silicone T-resin co-gellant level of about 5.5 to about 6.5% by weight, including 5.9% by weight. In exemplary embodiments, the ratio of ETPEA polymer to ester oils will be less than 1:40 or less than 1:50. Of course the ratio of ETPA polymer to oil will be limited, at the low end, by the point at which the amount of oil is so large that it solubilizes the polymer rather than forms a gel. At the high end of the ratio, gels of suitable firmness have been obtained with a weight ratio of ETPEA polymer to ester oils of about 1:1.3 or less (Sample 8 and 9) provided that suitable adjustments to the levels of other functional components are made.

Samples 6 and 7 show the effect of increasing ETPEA content in formulations having a lower silicone T-resin content than in Samples 2 and 3. In Samples 6 and 7, the silicone T-resin content is 2% by weight as compared to 5.9% by weight in Samples 2 and 3. As with Samples 2 and 3, it was similarly found that the firmness of the gel decreases with increasing ETPEA content from 109 g at 4.9% (Sample 7) to 43 g at 12% (Sample 6). The latter hardness value being only marginally above the hardness threshold of 40 g for making self-supporting solid sticks. The weight ratio ETPEA polymer to ester oils is about 1:3.75 in Sample 6 and about 1:10 in Sample 7. Again, even at a low silicone T-resin content of 2% by weight, a 1:10 ratio of ETPEA polymer to ester oils was found to provide suitable gels. At a ratio of 1:3.75 the gel exhibited a less desirable firmness, although it was above the 40 g hardness cut-off. Thus, in embodiments containing low amounts of silicone T-resin, i.e., less than about 5% by weight, and particularly less than about 3% by weight, suitable gels are obtained with a ratio of ETPEA to ester oils of less than about 1:3.75, more typically less than about 1:4 and preferably, about 1:10 or less.

Between Samples 4 and 5 it may generally be observed that the firmness of the gel improves with increasing wax content at the same weight percentages of ETPEA, silicone T-resin, and pigment/pearls. These samples range in total wax content from 6.85% to 9.6% with a corresponding increase in hardness from 117 g to 174 g. This result is not surprising as the waxy components are known to provide stiffness in traditional wax-based lipsticks. However, in the preferred practice of the invention, it is desirable not to exceed 12% by weight wax content as the waxes can mute the gloss of the product.

Sample 10 provides a very firm gel (413 g) made with a very low, 0.88% by weight, content of ETPEA polymer. The ratio of ETPEA gellant to ester oils is than 1:50. The remarkable firmness of this gel results in part from the high content of silicone T-resin gellant.

As evident from Table 6, gels of suitable hardness can be obtained over a wide range of ETPEA, wax, oil, silicone T-resin, and pigment/pearl contents. In embodiments where the compositions are to be formulated as a self-supporting stick, the compositions will have a hardness above 40 g. Typically, the compositions will have a hardness above about 50 g and more typically above about 60 g. Preferably, the compositions will have a hardness above about 70 g, 80 g, 90 g or 100 g. In some embodiments, the hardness of the compositions will be at least 120 g, 140 g, 160 g, 180 g, or 200 g. In other embodiments, the compositions will have a hardness of at least 250 g, 300 g, 350 g; or 400 g.

Example IV

In one aspect, the inventive compositions provide a unique rheology not obtainable with conventional wax-based lipsticks. The rheology is characterized by a perception that the lipstick retains a freshly applied feeling on the lips over a long period of wear, meaning that the feeling of the lipstick remains unctuous over that time. This example quantifies the unique rheology based on viscosity measurements over repeated shear cycles.

The conventional wax-based lipstick studied in this example has the formulation provided in Table 7.

TABLE 7

Wax-Based Lipstick

| Weight % | Component | Function |
|---|---|---|
| 5.00 | Micro Wax White | Wax |
| 3.00 | Polyethylene-Linear Pl | Wax |
| 5.50 | Ozokerite 170-D | Wax |
| 2.50 | Stearyl Dimethicone | Wax |
| 10.50 | Diglyceryl Diisostearate | Esters |
| 8.00 | Glyceryl Triacetyl Hydroxystearate | Esters |
| 3.00 | Polyglycerol Diisostearate | Esters |
| 7.50 | Myristyl Lactate | Esters |
| 4.50 | C10-30 Cholesterol | Esters |
| 10.00 | Squalane | Oil |
| 20.46 | Caster Oil | Oil |
| 3.20 | Polybutene | Film former |
| 0.12 | Acrylate Copolymer E0603 | Film former |
| 2.50 | PPG-51/SMDI Copolymer | |

TABLE 7-continued

Wax-Based Lipstick

| Weight % | Component | Function |
|---|---|---|
| 1.00 | Nylon Powder | Slip Aid |
| 0.50 | Silica High Absorbing | Particulate based gelling agent |
| 0.50 | Caprylyl Glycol | Preservative |
| 10.85 | Colorants | Colorants |
| 1.25 | Pearls And Mica | Reflective Pearls |
| 0.12 | Fragrance | Fragrance |

The ETPEA gel-based lipstick according to the invention employed in this example has the formulation provided in Table 8.

TABLE 8

ETPEA Gel-Based Lipstick

| Weight % | Component | Function |
|---|---|---|
| 8.00 | Polyethylene-Linear Pl | high melting wax 95° C. |
| 4.00 | Carnauba Wax | Low Melting wax |
| 18.00 | SYLVACLEAR ® C75V | ETPEA gellant |
| 0.10 | Polyphenylsilsesquioxane | Silicone T-resin gellant |
| 5.00 | Jojoba Oil/Gellants/Bht | Hydrocarbon gellant |
| 1.75 | Isopropyl Isostearate | Ester |
| 4.70 | Diisostearyl Fumarate | Ester |
| 10.00 | Isohexadecane | Hydrocarbon Based Oil |
| 9.95 | Hydrogenated Polyisobutene | Hydrocarbon Based Oil |
| 2.62 | Castor Oil Preserved | Hydrocarbon Based Oil |
| 3.14 | Octyldodecanol | Hydrocarbon Based Oil |
| 0.60 | PERFLUOROPOLY (ME) (ISOPR) ETH HC04 | Silicon Based Oil |
| 1.00 | Perfluorononyl Dimethicone - Hi Mw | Silicon Based Oil |
| 3.14 | Diphenyl Dimethicone | Silicon Based Oil |
| 5.00 | Sucrose Acetate Isobutyrate | Film Former |
| 1.00 | Acrylates Copolymer/Isododecane | Film Former |
| 0.50 | Glyceryl Rosinate-Food Grade | Film Former |
| 5.24 | Lanolin Acetate | Film Former |
| 7.00 | Ethylhexyl-Methoxycinnamate | Sunscreen |
| 2.00 | Octocrylene | Sunscreen |
| 0.50 | Caprylyl Glycol | Preservative |
| 0.01 | Sucralose | Sweetener |
| 5.83 | Pigments & Pearls | Colorants |
| 0.15 | Fragrance | Fragrance |

Figure 4:
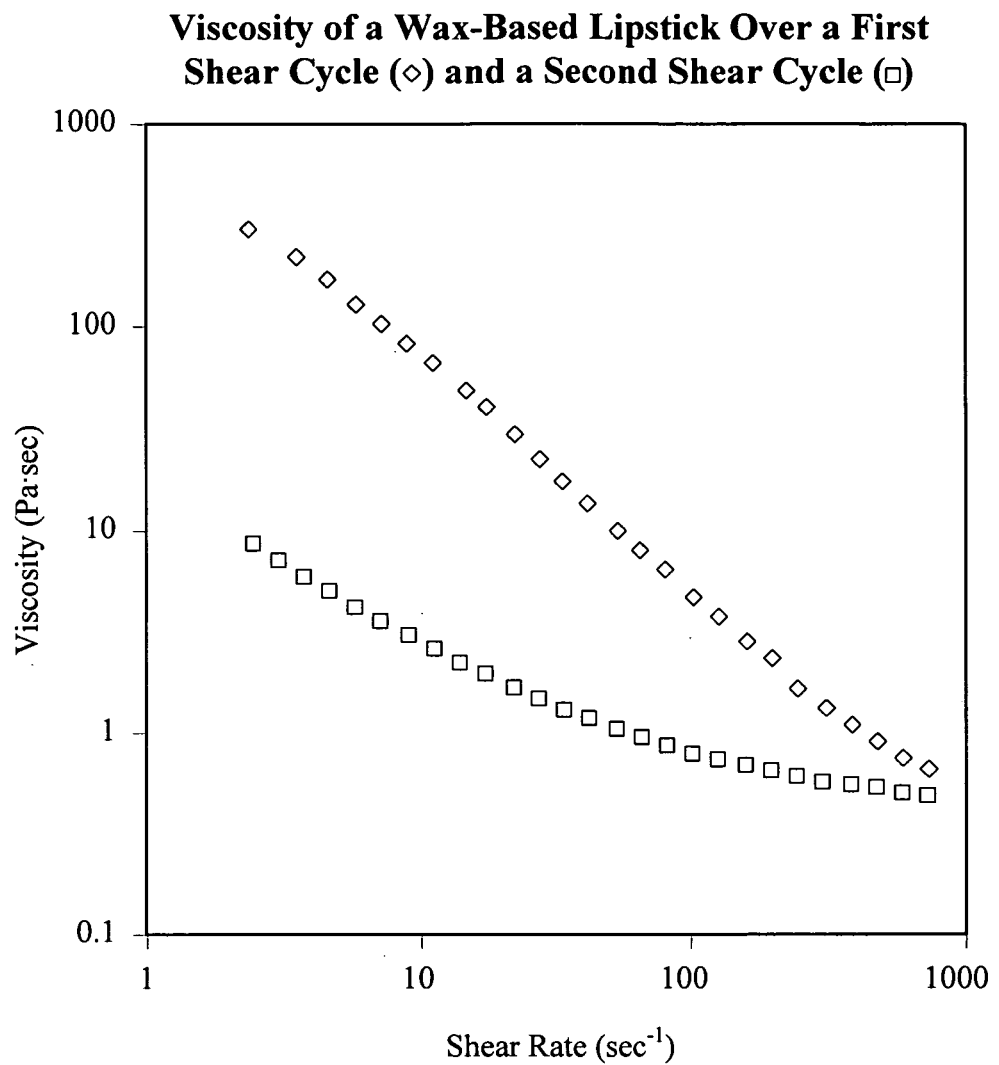
FIG. 4 shows the viscosity of a conventional wax-based lipstick as a function of shear rate over a first shear cycle (◊) and a second shear cycle (□).

FIG. 4 shows the viscosity of a conventional wax-based lipstick over a first shear cycle (◇) and a second shear cycle (□). As can be seen, the viscosity of the composition is a function of shear rate, such that the viscosity of the composition decreases during the first shear cycle of the entire range of shear rates. Notably, during the second shear cycle, the composition does not retain the initial viscosity achieved at the onset of the first shear cycle. Rather, the viscosity is seen to fall to less than 10 Pa·sec at the beginning of the second shear cycle to less than 1 Pa·sec at the end of the second shear cycle. The viscosity loss seen throughout the second shear cycle is the results of the degradation of the wax structure during the first shear cycle.

Figure 5:
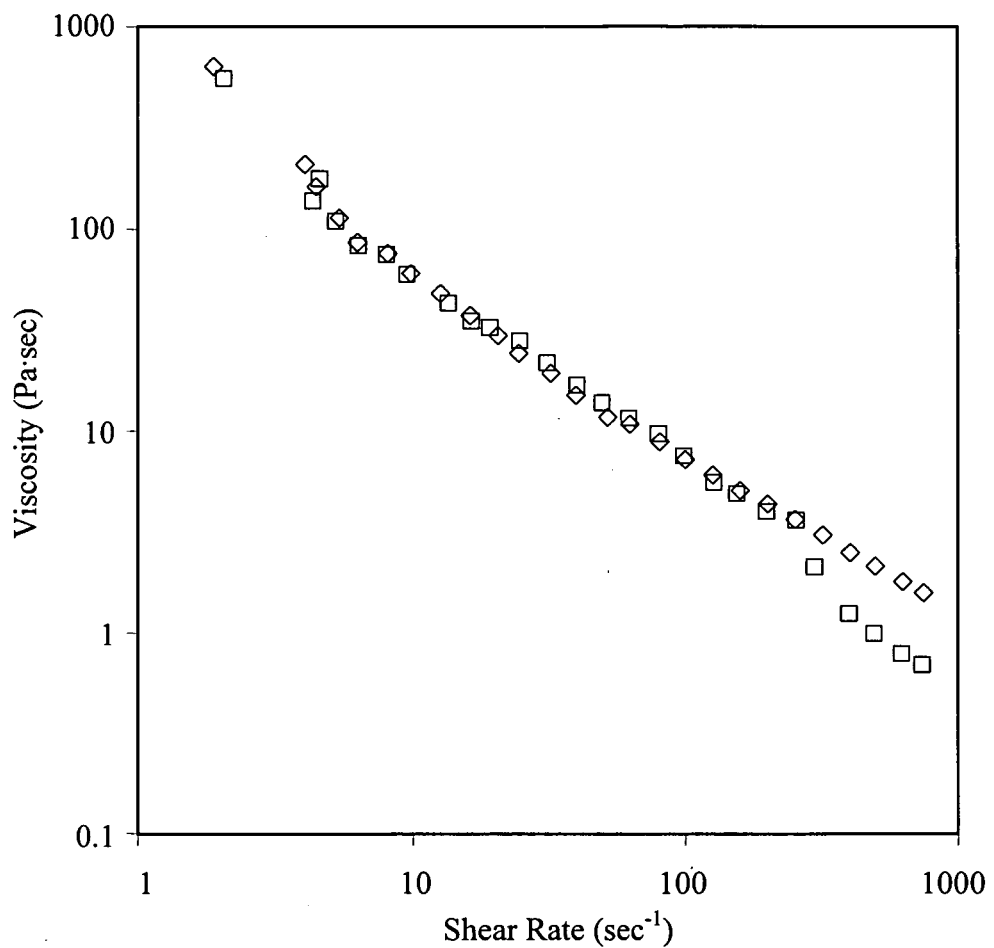
FIG. 5 shows the viscosity of an ETPEA gel-based lipstick as a function of shear rate over a first shear cycle (◊) and a second shear cycle (□).

FIG. 5 shows the viscosity of a lipstick according to the invention over a first shear cycle (◇) and a second shear cycle (□). The viscosity over the first and second shear cycles remain nearly identical over the entire range of shear rates. While some deviation is seen during the second shear cycle at very high shear rates, the deviation is minimal over the range of shear rates from 1 to 10 $sec^{-1}$ which corresponds to shear rates typically encountered during wear. This resistance to shear induced degradation is believed to result from the elastic nature of the gel such that hydrogen bonds are broken to accommodate shear and reformed to restore the gel-network when the shear is released.

The lipstick of the invention shown in FIG. 5 was found to have an oily, moisturizing feeling when initially applied and to retain that feeling through repeated cycles of rubbing the lips together over time.

All patents and patent publications referred to herein are hereby incorporated by reference.

Certain modifications and improvements will occur to those skilled in the art upon a reading of the foregoing description. It should be understood that all such modifications and improvements have been deleted herein for the sake of conciseness and readability but are properly within the scope of the following claims.

The invention claimed is:

1. A method for imparting an unctuous film to the lips comprising applying thereto a composition comprising:
    (a) from 0.1 to 2.5% by weight of Bis-Stearyl Ethylenediamine/Neopentyl Glycol/Stearyl Hydrogenated Dimer Dilinoleate copolymer having an average molecular weight between 3,000 and 7,500 Daltons and being capable of forming a gel with low-polarity and nonpolar oils at or below a sol-gel transition temperature $T_{gel}$ wherein $T_{gel}$ is above body temperature;
    (b) from 5 to 12% by weight of a first wax component comprising linear polyethylene and microcrystalline petroleum wax having a melting point above $T_{gel}$; wherein said first wax component equals or exceeds, on a weight basis, the amount of said Bis-Stearyl Ethylenediamine/Neopentyl Glycol/Stearyl Hydrogenated Dimer Dilinoleate copolymer;
    (c) from 5 to 12% by weight of a second wax component comprising ozokerite and lanolin having a melting point at or below $T_{gel}$; and
    (d) from 40 to 80% by weight of one or more low-polarity or nonpolar ester oils capable of forming a gel with said Bis-Stearyl Ethylenediamine/Neopentyl Glycol/Stearyl Hydrogenated Dimer Dilinoleate copolymer at or below said sol-gel transition temperature $T_{gel}$; wherein the weight ratio of Bis-Stearyl Ethylenediamine/Neopentyl Glycol/Stearyl Hydrogenated Dimer Dilinoleate copolymer to said ester oils is less than 1:30; wherein said ester oils comprise an oil selected from triisostearoyl polyglyceryl-3 dimer dilinoleate, diisopropyl dimerate, triisostearyl trilinoleate, $C_{12-15}$ alcohols benzoate, octyldodecyl stearoyl stearate, diisostearyl fumarate, polyglyceryl-2 diisostearate/IPDI copolymer, and combinations thereof;
wherein said composition is self-supporting at room temperature and is further characterized by a viscosity measured during a second shear cycle that is within ±20% of the viscosity measured during a first shear cycle at every shear rate between 1 and 10 $sec^{-1}$, wherein said first and said second shear cycles are identical and comprise increasing shear rates from 1 to 1,000 $sec^{-1}$.

2. The method of claim 1 wherein the viscosity measured in said second shear cycle is within ±10% of the viscosity measured during said first shear cycle at every shear rate between 1 and 10 $sec^{-1}$.

3. The method of claim 1 wherein the viscosity measured in said second shear cycle is within ±5% of the viscosity measured during said first shear cycle at every shear rate between 1 and 10 $sec^{-1}$.

4. The method of claim 1 further characterized by a viscosity measured during said second shear cycle that is within ±20% of the viscosity measured during said first shear cycle at every shear rate between 10 and 100 $sec^{-1}$.

5. The method of claim 4 wherein the viscosity measured in said second shear cycle is within ±10% of the viscosity measured during said first shear cycle at every shear rate between 10 and 100 sec$^{-1}$.

6. The method of claim 4 wherein the viscosity measured in said second shear cycle is within ±5% of the viscosity measured during said first shear cycle at every shear rate between 10 and 100 sec$^{-1}$.

7. The method of claim 1 further characterized by a viscosity greater than 50 Pa·sec at a shear rate of 1 sec$^{-1}$ as measured during said first shear cycle.

8. The method of claim 1 further characterized by a viscosity greater than 75 Pa·sec at a shear rate of 1 sec$^{-1}$ as measured during said first shear cycle.

9. The method of claim 1 further characterized by a viscosity greater than 100 Pa·sec at a shear rate of 1 sec$^{-1}$ as measured during said first shear cycle.

10. The method of claim 1 further characterized by a viscosity greater than 50 Pa·sec at a shear rate of 1 sec$^{-1}$ as measured during said first and said second shear cycles.

11. The method of claim 1 further characterized by a viscosity greater than 75 Pa·sec at a shear rate of 1 sec$^{-1}$ as measured during said first and said second shear cycles.

12. The method of claim 1 further characterized by a viscosity greater than 100 Pa·sec at a shear rate of 1 sec$^{-1}$ as measured during said first and said second shear cycles.

13. The method of claim 1 further characterized by a viscosity greater than 50 Pa·sec at shear rates from 1 to 5 sec$^{-1}$ as measured during said first shear cycle.

14. The method of claim 1 further characterized by a viscosity greater than 75 Pa·sec at shear rates from 1 to 5 sec$^{-1}$ as measured during said first shear cycle.

15. The method of claim 1 further characterized by a viscosity greater than 100 Pa·sec at shear rates from 1 to 5 sec$^{-1}$ as measured during said first shear cycle.

16. The method of claim 1 further characterized by a viscosity greater than 50 Pa·sec at shear rates from 1 to 5 sec$^{-1}$ as measured during said first and said second shear cycles.

17. The method of claim 1 further characterized by a viscosity greater than 75 Pa·sec at shear rates from 1 to 5 sec$^{-1}$ as measured during said first and said second shear cycles.

18. The method of claim 1 further characterized by a viscosity greater than 100 Pa·sec at shear rates from 1 to 5 sec$^{-1}$ as measured during said first and said second shear cycles.

19. The method of claim 1 further characterized by a viscosity greater than 5 Pa·sec at a shear rate of 10 sec$^{-1}$ as measured during said first shear cycle.

20. The method of claim 1 further characterized by a viscosity greater than 7.5 Pa·sec at a shear rate of 10 sec$^{-1}$ as measured during said first shear cycle.

21. The method of claim 1 further characterized by a viscosity greater than 10 Pa·sec at a shear rate of 10 sec$^{-1}$ as measured during said first shear cycle.

22. The method of claim 1 further characterized by a viscosity greater than 5 Pa·sec at a shear rate of 10 sec$^{-1}$ as measured during said first and said second shear cycles.

23. The method of claim 1 further characterized by a viscosity greater than 7.5 Pa·sec at a shear rate of 10 sec$^{-1}$ as measured during said first and said second shear cycles.

24. The method of claim 1 further characterized by a viscosity greater than 10 Pa·sec at a shear rate of 10 sec$^{-1}$ as measured during said first and said second shear cycles.

25. The method of claim 1 further characterized by a viscosity greater than 5 Pa·sec at a shear rate from 10 to 50 sec$^{-1}$ as measured during said first shear cycle.

26. The method of claim 1 further characterized by a viscosity greater than 7.5 Pa·sec at a shear rate from 10 to 50 sec$^{-1}$ as measured during said first shear cycle.

27. The method of claim 1 further characterized by a viscosity greater than 10 Pa·sec at a shear rate from 10 to 50 sec$^{-1}$ as measured during said first shear cycle.

28. The method of claim 1 further characterized by a viscosity greater than 5 Pa·sec at a shear rate from 10 to 50 sec$^{-1}$ as measured during said first and said second shear cycles.

29. The method of claim 1 further characterized by a viscosity greater than 7.5 Pa·sec at a shear rate from 10 to 50 sec$^{-1}$ as measured during said first and said second shear cycles.

30. The method of claim 1 further characterized by a viscosity greater than 10 Pa·sec at a shear rate from 10 to 50 sec$^{-1}$ as measured during said first and said second shear cycles.

31. The method of claim 1 wherein said composition has a viscosity greater than 0.5 Pa·sec at a shear rate of 100 sec$^{-1}$ as measured during said first shear cycle.

32. The method of claim 1 wherein said composition has a viscosity greater than 0.75 Pa·sec at a shear rate of 100 sec$^{-1}$ as measured during said first shear cycle.

33. The method of claim 1 wherein said composition has a viscosity greater than 1 Pa·sec at a shear rate of 100 sec$^{-1}$ as measured during said first shear cycle.

34. The method of claim 1 wherein said composition has a viscosity greater than 0.5 Pa·sec at a shear rate of 100 sec$^{-1}$ as measured during said first and said second shear cycles.

35. The method of claim 1 wherein said composition has a viscosity greater than 0.75 Pa·sec at a shear rate of 100 sec$^{-1}$ as measured during said first and said second shear cycles.

36. The method of claim 1 wherein said composition has a viscosity greater than 1 Pa·sec at a shear rate of 100 sec$^{-1}$ as measured during said first and said second shear cycles.

37. The method of claim 1 further comprising a silicone T-resin.

38. The method of claim 37 wherein said silicone T-resin comprises siloxy moieties of the form:

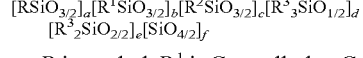

where R is methyl; $R^1$ is $C_{2-20}$ alkyl or $C_{5-20}$ cycloalkyl; $R^2$ is phenyl, $R^3$ is $C_{1-20}$ alkyl, $C_{5-20}$ cycloalkyl, $C_{7-14}$ aralkyl, $C_{7-14}$ alkaryl, or $C_{6-10}$ aryl; and a, b, and c are such that their respective siloxy groups together comprise at least 90 mol percent of the total of siloxy moieties, and d, e, and f are such that their respective moieties together comprise less than 10 mol percent of all of siloxy moieties.

39. The method of claim 37 wherein said silicone T-resin is a polyphenylsilsesquioxane.

40. The method of claim 37 wherein said silicone T-resin has a refractive index of at least 1.5, measured as a film at 25° C.

41. The method of claim 7 wherein the average molecular weight of said silicone T-resin is between 5,000 and 6,000 Daltons.

42. The method of claim 1 wherein said sol-gel transition temperature $T_{gel}$ of said ester terminated poly(ester-amide) polymer is 70 to 85° C. and said composition has a hardness of at least 40 g.

43. The method of claim 1 wherein said sol-gel transition temperature $T_{gel}$ is 75° C.

44. The method of claim 1, wherein said Stearyl Ethylenediamine/Neopentyl Glycol/Stearyl Hydrogenated Dimer Dilinoleate copolymer comprises between 1 and 2.5% by weight of said composition and said first and second wax components collectively comprise between 5 and 12% by weight of said composition.

45. The method of claim 37, wherein said Stearyl Ethylenediamine/Neopentyl Glycol/Stearyl Hydrogenated Dimer Dilinoleate copolymer comprises between 1 and 2.5% by weight of said composition, said first and second wax components collectively comprise between 10 and less than 12% by weight of said composition, and said silicone T-resin comprises between 0.1 and 8% by weight of said composition.

46. A method for imparting an unctuous film to the lips comprising applying thereto a composition comprising:
   (a) from 0.1 to 2.5% by weight Bis-Stearyl Ethylenediamine/Neopentyl Glycol/Stearyl Hydrogenated Dimer Dilinoleate copolymer having an average molecular weight between 3,500 and 7,000 Daltons and being capable of forming a gel with low-polarity and nonpolar oils at or below a sol-gel transition temperature $T_{gel}$ of 70° C. to 85° C.;
   (b) from 5 to 12% by weight of a first wax component comprising linear polyethylene and microcrystalline petroleum wax having a melting point above $T_{gel}$; wherein said first wax component equals or exceeds, on a weight basis, the amount of Bis-Stearyl Ethylenediamine/Neopentyl Glycol/Stearyl Hydrogenated Dimer Dilinoleate copolymer;
   (c) from 5 to 12% by weight of a second wax component comprising ozokerite and lanolin having a melting point at or below $T_{gel}$; and
   (d) from 40 to 80% by weight of one or more low-polarity or nonpolar ester oils capable of forming a gel with said ester terminated poly(ester-amide) polymer at or below said sol-gel transition temperature $T_{gel}$; wherein the weight ratio of Bis-Stearyl Ethylenediamine/Neopentyl Glycol/Stearyl Hydrogenated Dimer Dilinoleate copolymer to said ester oils is less than 1:30; wherein said ester oils comprise an oil selected from triisostearoyl polyglyceryl-3 dimer dilinoleate, diisopropyl dimerate, triisostearyl trilinoleate, $C_{12-15}$ alcohols benzoate, octyldodecyl stearoyl stearate, diisostearyl fumarate, polyglyceryl-2 diisostearate/IPDI copolymer, and combinations thereof;

wherein said composition is self-supporting at room temperature and is further characterized by a viscosity measured during a second shear cycle that is within ±20% of the viscosity measured during a first shear cycle at every shear rate between 1 and 10 $sec^{-1}$, wherein said first and said second shear cycles are identical and comprise increasing shear rates from 1 to 1,000 $sec^{-1}$; and wherein said composition is characterized by:
   (i) a viscosity greater than 100 Pa·sec at shear rates between 1 and 5 $sec^{-1}$ when measured during said first and second shear cycles; and
   (ii) a viscosity greater than 10 Pa·sec at shear rates between 10 and 50 $sec^{-1}$ when measured during said first and second shear cycles; and
   (iii) a viscosity greater than 1 Pa·sec at a shear rate of 100 $sec^{-1}$ when measured during said first and second shear cycles.

47. The method of claim 46 further comprising from about 0.1 to about 8% by weight of a silicone T-resin.

48. The method of claim 47 wherein said silicone T-resin is a polyphenylsilsesquioxane.

49. The method of claim 45 wherein the silicone T-resin is a polyphenylsilsesquioxane.

* * * * *